(12) United States Patent
Liotta et al.

(10) Patent No.: US 10,688,112 B2
(45) Date of Patent: Jun. 23, 2020

(54) LIPID DISULFIDE PRODRUGS AND USES RELATED THERETO

(71) Applicant: Emory University, Atlanta, GA (US)

(72) Inventors: Dennis Liotta, Atlanta, GA (US); Kyle Giesler, Winter Springs, FL (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 16/035,164

(22) Filed: Jul. 13, 2018

(65) Prior Publication Data

US 2019/0015432 A1 Jan. 17, 2019

Related U.S. Application Data

(60) Provisional application No. 62/532,013, filed on Jul. 13, 2017.

(51) Int. Cl.

| A61K 31/661 | (2006.01) |
|---|---|
| A61K 9/12 | (2006.01) |
| A61K 9/127 | (2006.01) |
| A61K 9/20 | (2006.01) |
| A61P 31/12 | (2006.01) |
| A61P 35/00 | (2006.01) |
| A61K 45/06 | (2006.01) |
| A61K 47/54 | (2017.01) |
| A61K 31/20 | (2006.01) |
| A61K 31/52 | (2006.01) |

(52) U.S. Cl.
CPC .............. *A61K 31/661* (2013.01); *A61K 9/12* (2013.01); *A61K 9/127* (2013.01); *A61K 9/2013* (2013.01); *A61K 45/06* (2013.01); *A61K 47/543* (2017.08); *A61P 31/12* (2018.01); *A61P 35/00* (2018.01); *A61K 31/20* (2013.01); *A61K 31/52* (2013.01); *A61K 2300/00* (2013.01)

(58) Field of Classification Search
CPC .................................................. A61K 31/661
See application file for complete search history.

(56) References Cited

U.S. PATENT DOCUMENTS

| 5,770,725 A | 6/1998 | Gosselin et al. |
|---|---|---|
| 5,849,905 A * | 12/1998 | Gosselin .............. C07F 9/65616 536/26.7 |
| 6,020,482 A | 2/2000 | Gosselin et al. |
| 6,555,676 B2 | 4/2003 | Gosselin et al. |
| 7,902,202 B2 | 3/2011 | Sommadossi et al. |
| 8,871,785 B2 | 10/2014 | Boojamra et al. |

| 2010/0298256 A1 | 11/2010 | Dong et al. | |
|---|---|---|---|
| 2012/0164230 A1* | 6/2012 | Feazell ................ | A61K 31/282 424/490 |
| 2015/0291639 A1 | 10/2015 | Phull et al. | |

FOREIGN PATENT DOCUMENTS

| WO | 2015038596 | 3/2015 | |
|---|---|---|---|
| WO | WO-2016044281 A1 * | 3/2016 | ............... A61K 8/24 |

OTHER PUBLICATIONS

"Pharmaceutical Dosage Forms, Tablets" Edited by Lieberman, Lachman and Schwartz, Second Edition in Three Volumes, vol. 1, Marcel Dekker: New York, 1989.*
Dorwald F. A. Side Reactions in Organic Synthesis, 2005, Wiley: VCH, Weinheim p. IX of Preface p. 1-15.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Rautio et. al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Wisclicenus, J. "Adolph Strecker's Short Textbook of Organic Chemistry" 1881, Spottiswoode: London, pp. 38-39.*
Henze, "The Number of Structurally Isomeric Alcohols of the Methanol Series" Journal of the American Chemical Society 1931, 53(8), 3042-3046.*
Giesler et al. Reduction Sensitive Lipid Conjugates of Tenofovir: Synthesis, Stability, and Antiviral Activity, J. Med. Chem. 2016, 59 (15) 7097-7110.
Giesler et al. Next-Generation Reduction Sensitive Lipid Conjugates of Tenofovir: Antiviral Activity and Mechanism of Release, J Med Chem. Nov. 23, 2016;59(22)10244-10252.
Pradere, U. et al. Synthesis of Nucleoside Phosphate and Phosphonate Prodrugs, Chemical Reviews, 2014, 114, 9154-9218.

* cited by examiner

*Primary Examiner* — David K O'Dell
(74) *Attorney, Agent, or Firm* — Emory Patent Group

(57) ABSTRACT

This disclosure relates to lipid disulfide prodrugs and in particular to lipid disulfide phosphodiester nucleosides and derivatives thereof, pharmaceutical compositions, and uses related thereto. According to one embodiment of the disclosure there is provided a compound of Formula I,

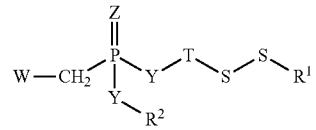

Formula I or pharmaceutically acceptable salts or derivatives thereof, wherein substitutents are disclosed herein.

12 Claims, 3 Drawing Sheets

Tenofovir-Alafenamide
(TAF)

Hexadecyloxypropyl-Tenofovir
(CMX-157)

R= alkyl or -CH₂CH₂SSCH₂CH₂OH

W = Any biologically active
     compound, e.g.
     nucleoside etc.
T = Any linking spacer,
     e.g. $C_2$-$C_4$ alkyl chain,
     benzyl, etc.
$R^1$ = any lipid, e.g. $C_6$-$C_{20}$
     alkyl chain, etc.

e.g.

LIPID DISULFIDE PRODRUGS AND USES RELATED THERETO

CROSS-REFERENCE TO RELATED APPLICATIONS

This application claims the benefit of U.S. Provisional Application No. 62/532,013 filed Jul. 13, 2017. The entirety of this application is hereby incorporated by reference for all purposes.

BACKGROUND

Many drug candidates and natural products are flanked with structural features such as carboxylic acids, amines, dianionic phosphates and polyhydroxylated aromatic rings, etc. that may limit their therapeutic potential in vivo. Such features often require temporary protection with a prodrug to improve the absorption, distribution, metabolism and excretion (ADME) properties of a pharmacologically active compound within the body.

One example is Tenofovir (TFV), which is an acyclic nucleoside with anti-viral activity against human immunodeficiency virus (HIV), hepatitis B virus (HBV), and herpes simplex type-2 virus (HSV-2). TFV structurally resembles 2',3'-dideoxyadenosine which lacks the requisite 3' hydroxyl moiety necessary for DNA polymerization and triggers obligate chain termination upon incorporation of tenofovir diphosphate (TFVdpp) into the growing viral DNA strand. A common structural feature amongst acyclic nucleosides (e.g. TFV, adefovir, cidofovir, ganciclovir, etc.) is a catabolically stable phosphonate linkage that permanently affixes the phosphonate to the acyclic sugar linker and nucleobase. This serves to prevent undesirable chemical and enzymatic hydrolysis and bypasses the initial phosphorylation to the monophosphate, which is the kinetic bottleneck during the conversion of conventional nucleosides to their active triphosphate (De Clercq et al., Nature reviews. Drug discovery, 2005, 4, 928).

The dianionic character of TFV and other acyclic nucleosides at physiological pH restricts diffusion across the plasma membrane resulting in rapid renal clearance and depreciated bioavailability and antiviral activity. When orally administered to mice, the bioavailability of TFV is approximately 2% and that of adefovir has been reported to be <1% in monkeys and 8-11% in rats (see Kearney et al., J. Clin. Pharmacokinet., 2004, 43, 595, Balzarini et al. AIDS, 1991, 5, 21. Starrett et al., J. Med. Chem., 1994, 37, 1857). These undesirable properties can be ameliorated by masking the anionic phosphonic acid with various prodrugs that alter the pharmacokinetic profile of the parent nucleoside, enhance cellular permeability, and improve bioavailability. Several eclectic prodrug strategies have been developed for this purpose.

The clinically-approved prodrug formulation of TFV is tenofovir disoproxil fumarate (TDF), manufactured by Gilead Sciences under the trade name Viread®, which features two isopropyloxymethyl carbonate masking units esterified to the phosphonate that relies on an esterase-activated cleavage mechanism to liberate TFV following successful delivery to the target tissue. The installation of two isopropyl carbonate esters increases the oral bioavailability of TFV to 25%, dramatically enhances tissue distribution and improves biological stability. However, the ubiquitous distribution of esterases renders a significant fraction of TDF susceptible to premature hydrolysis resulting in systemic exposure to TFV, a known nephrotoxin, potentially causing undesirable side effects (see Karras et al. Clinical infectious diseases: an official publication of the Infectious Diseases Society of America, 2003, 36, 1070). Continuous administration of TDF has been reported to induce lactic acidosis, Fanconi syndrome, acute renal failure, and bone loss, all of which stem from mitochondrial toxicity (see Fernandez et al., AIDS Res. Treat.; 2011: 354908 and Coca & Perazella, American Journal of the Medical Sciences, 2002, 324(6):342-344).

Other candidates surfaced in clinical trials are Tenofovir-Alafenamide (TAF) and Hexadecyloxypropyl-Tenofovir (CMX-157), as illustrated in FIG. 1. TAF is an isopropyl-alaninyl phenyl ester that requires two disparate enzymes for prodrug release: carboxyesterase and cathepsin A. The latter enzyme, cathepsin A, is a serine protease localized almost exclusively to lysosomal endosomes and ensures selective intracellular delivery of TFV. TAF is currently approved in the clinic and demonstrates little to no nephrotoxicity and more potent antiviral activity than TDF at $\frac{1}{10}$th the dose. Painter et al. reported evaluations of CMX-157 as a potential treatment for HIV type 1 and HBV infections (*Antimicrob. Agents Chemother.*, 2007, 51, 3505-3509). CMX-157 relies on the catalytic activity of an intracellular hydrolase-phospholipase C and/or sphingomylenase to liberate TFV within the cytosol. Available preliminary data indicates CMX-157 is well-tolerated and achieves significant concentrations of TFVdpp up to one week after a single 400 mg dose, indicating the potential for a convenient, once-a-week dosing regimen. However, CMX-157 has made little progression through the clinical trial pipeline since the completion of Phase I in 2011.

Gosselin and collaborators previously examined dithioethanol (DTE) conjugates to mediate the delivery of adefovir, AZT, and 3'-deoxyuridine (ddU) to HIV-1 infected cell lines in vitro. U.S. Pat. No. 6,020,482 reports phosphotriester type biologically active compounds and also see U.S. Pat. Nos. 6,555,676, 7,902,202, and 8,871,785.

Conjugation of bis(DTE) to adefovir increases the HIV-1 activity of the parent nucleoside by ten-fold and confers exceptional stability ($t_{1/2}$>24 h) at pH 2, pH 7.4, culture medium, and human gastric juice. However, these conjugates rapidly degrade in human serum ($t_{1/2}$<5 min) which significantly limits their clinical utility. A proposed cleavage mechanism for these masking groups is illustrated in FIG. 2. Reduction of compound (i) releases β-mercaptoethanol and metastable intermediate (ii) that spontaneously collapses on the thioethanol linker to generate thiirane and the free nucleoside (iii) (when R=H). It was speculated that the β-mercaptoethyl linker may be a precursor for thiirane which has been implicated in the decomposition of S-acyl-2-thioethyl (SATE) and dithioethanol (DTE) prodrugs. Of note, SATE prodrugs also pass through common intermediate (ii) following hydrolysis of an S-acyl moiety via non-specific carboxyesterases to liberate the target nucleoside. The apparent instability of the disulfide linkage in serum has stalled efforts to advance this technology forward and the mutagenic potential of thiirane has precluded the clinical use of SATE and DTE-bound nucleosides. References cited herein are not an admission of prior art.

Thus, there is a need to identify improvements and exploit alternative prodrug strategies to enhance intracellular delivery of pharmacologically active compounds, such as useful nucleosides like tenofovir.

SUMMARY

This disclosure relates to lipid disulfide prodrugs and in particular to lipid disulfide phosphodiester nucleosides and derivatives thereof, pharmaceutical compositions, and uses related thereto. According to one embodiment of the disclosure there is provided a compound of Formula I,

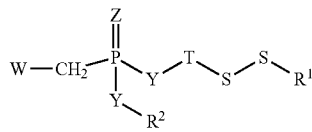

Formula I or pharmaceutically acceptable salts or derivatives thereof, wherein, W is a pharmacologically active compound, or linking group for connecting to a pharmacologically active compound; Z is selected from O, S, or Se; Y is selected from O, S, or NH; T is an aryl or alkyl linking group, $R^1$ is a lipid; $R^2$ is $R^1$SST-, hydrogen, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$;

$R^{10}$ is deuterium, alkyl, alkenyl, alkynyl, alkanoyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{10}$ is optionally substituted with one or more, the same or different, $R^{11}$; and $R^{11}$ is deuterium, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, benzyl, benzoyl, carbocyclyl, aryl, or heterocyclyl.

Further features of this embodiment provide for W to be a nucleoside or nucleobase or a linking group for connecting to a nucleoside or nucleobase; T to be a $C_2$ to $C_6$ alkyl or an aryl, and T may be optionally substituted with one or more, the same or different $R^{10}$; Z and Y are each O; $R^1$ is a $C_6$ to $C_{20}$ lipid; $R^2$ is $R^1$SST-, hydrogen, alkyl, aryl or phenyl. Yet further features of this embodiment provide for $R^1$ to be a $C_{10}$-$C_{18}$ lipid, preferably a $C_{16}$ to $C_{18}$ lipid, and more preferably a $C_{16}$ lipid and for $R^2$ to be H, methyl, or alkyl.

In another embodiment of the disclosure, there is provided a compound of Formula I'

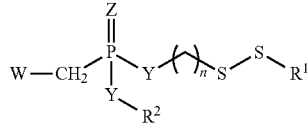

Formula I' or salts or derivatives thereof wherein, n is 2, 3, 4, 5 or 6; W is a nucleoside or linking group for connecting to a nucleoside or nucleobase; Z is selected from O, S, or Se; Y is selected from O, S, or NH; $R^1$ is a lipid; $R^2$ is $R^1$SS(CH$_2$)$_n$—, hydrogen, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$, as described above and which is optionally substituted with one or more, the same or different, $R^{11}$, as described above.

In another embodiment of the disclosure there is provided a compound of Formula I'',

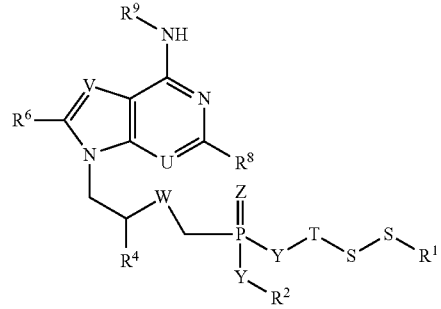

Formula I'' or salts or derivatives thereof wherein, T is —C$_6$H$_4$—, —(CH$_2$)$_n$—, —CH$_2$—C$_6$H$_4$—, a linking group providing an atomic chain of two, three or four atoms, —R$_m$—, wherein m is 1, 2, 3, or 4, or a bridging alkyl, alkenyl, optionally substituted carbocyclyl, optionally substituted heterocyclyl, optionally substituted aryl, substituted heterocyclyl; U is N or CH; V is N or CR$^7$; W is O or S; Z is selected from O, S, or Se; Y is selected from O, S, or NH; $R^1$ is a lipid; $R^2$ is $R^1$SST- or H; $R^4$ is hydrogen, alkyl, or halogen, wherein $R^4$ is optionally substituted with one or more, the same or different, $R^{10}$; $R^6$ is hydrogen, alkyl, amino, or halogen, wherein $R^6$ is optionally substituted with one or more, the same or different, $R^{10}$; $R^7$ is hydrogen, alkyl, or halogen, wherein $R^7$ is optionally substituted with one or more, the same or different, $R^{10}$; $R^8$ is hydrogen, alkyl, amino, or halogen, wherein $R^8$ is optionally substituted with one or more, the same or different, $R^{10}$; $R^9$ is hydrogen, alkyl, cyclopropyl, or carbocyclyl, wherein $R^9$ is optionally substituted with one or more, the same or different, $R^{10}$; $R^{10}$ is as described above and is optionally substituted with one or more, the same or different, $R^{11}$, as described above.

In a preferred embodiment of the disclosure the compound of Formula I may be selected from the following compounds as free acids, salts or derivatives thereof:

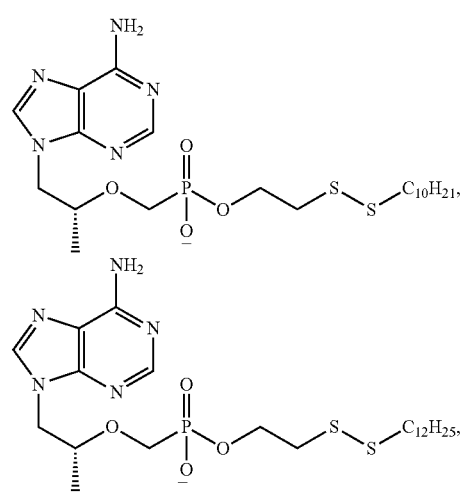

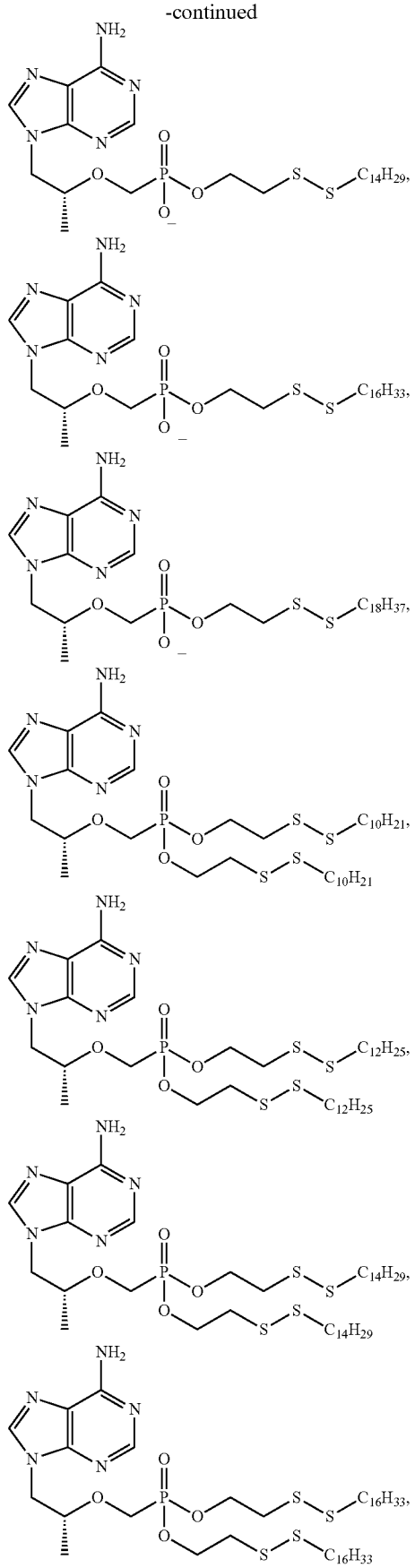
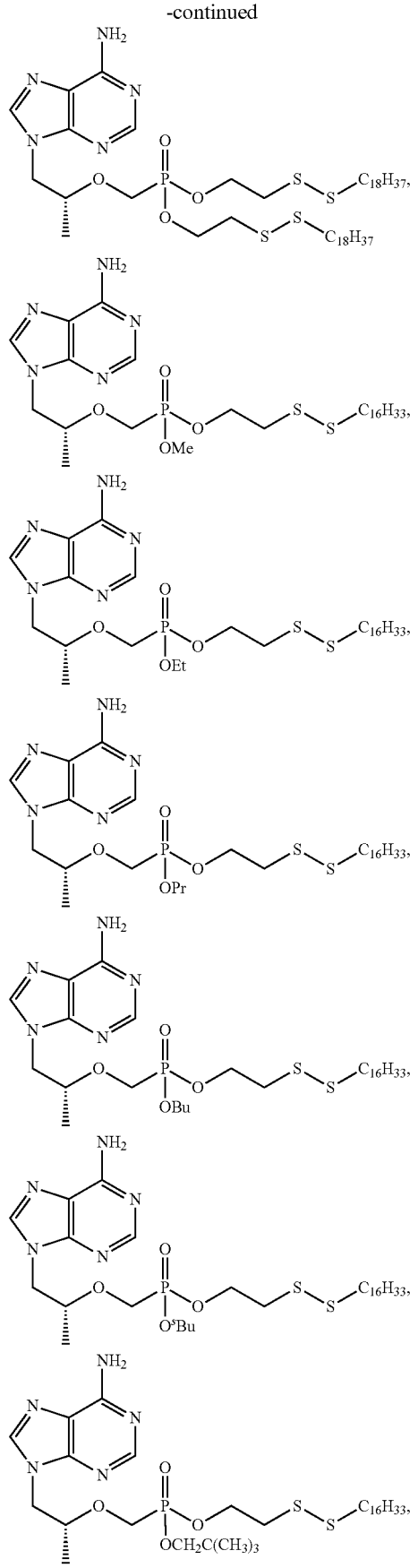

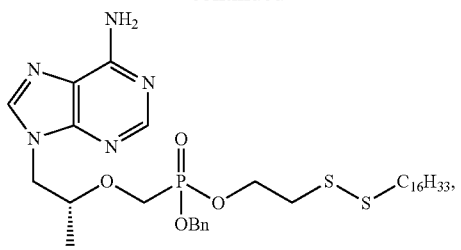
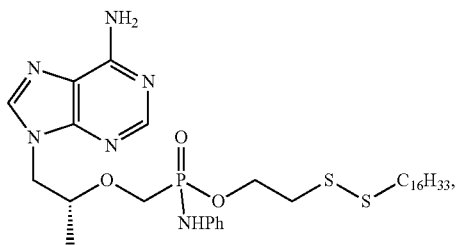
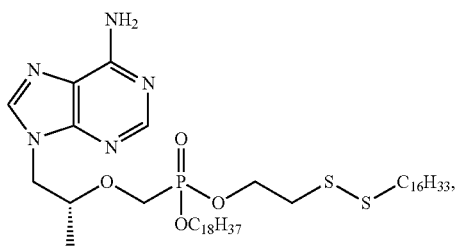
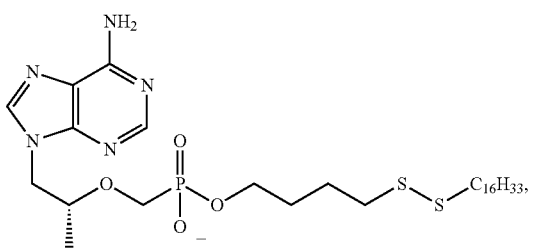
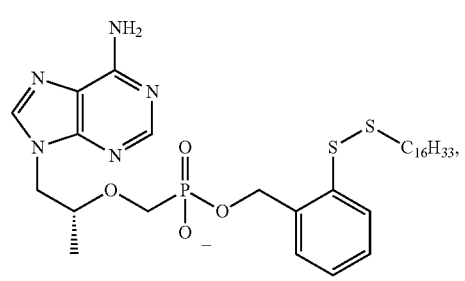
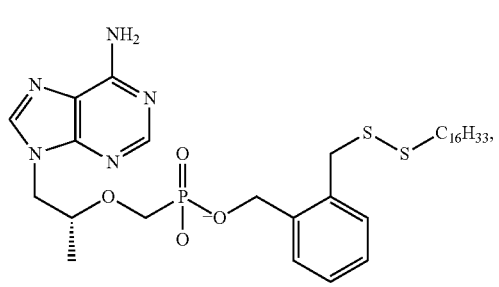
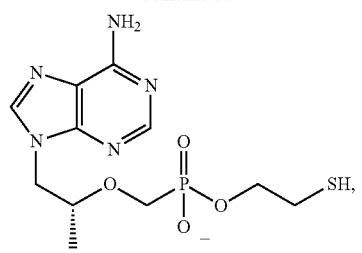
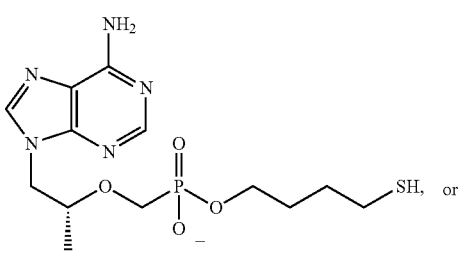
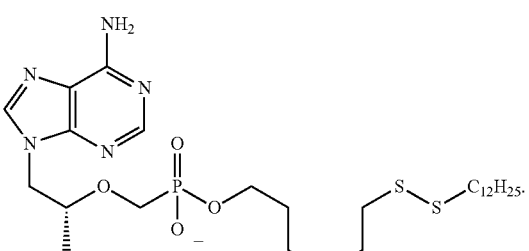
In a more preferred embodiment of the disclosure the compound of Formula I may be selected from the following compounds as free acids, salts, or derivatives thereof:
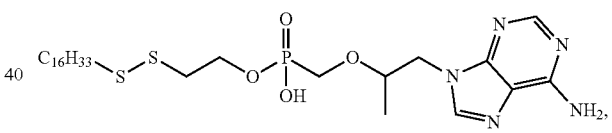
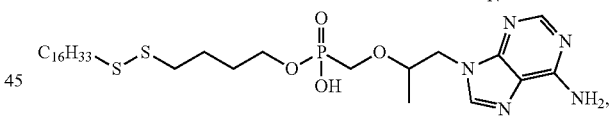
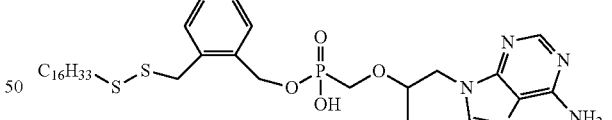
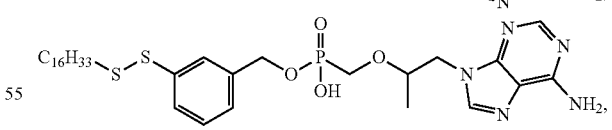
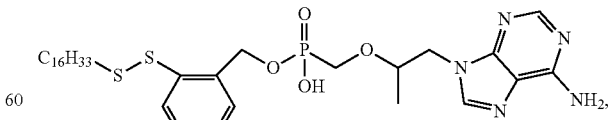
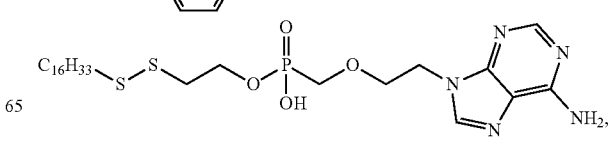

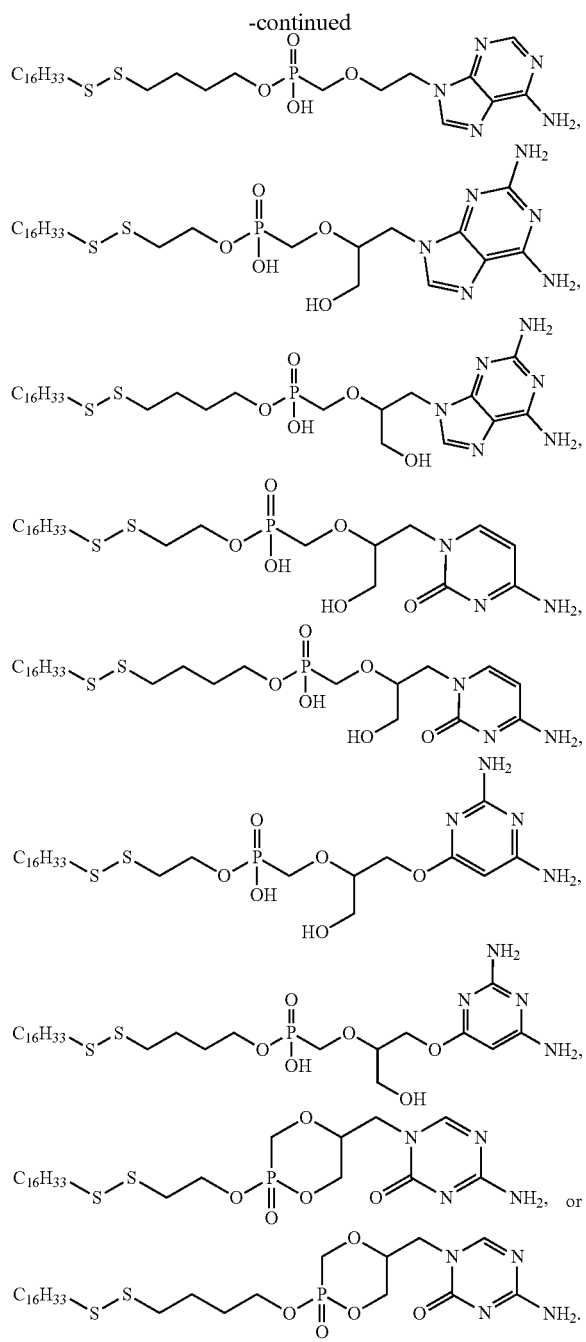

In a further embodiment of the disclosure there is provided a method of treating a viral infection comprising administering in effective amount of a compound as described above to a subject in need thereof.

In certain embodiments, the disclosure contemplates derivatives of compounds disclosed herein such as those containing one or more, the same or different, substituents.

In certain embodiments, the disclosure contemplates pharmaceutical compositions comprising a pharmaceutically acceptable excipient and a compound disclosed herein. In certain embodiments, the pharmaceutical composition is in the form of a tablet, capsule, pill, gel, granules, aerosol, or aqueous buffer, such as a saline or phosphate buffer, or a nanoparticle formulation, emulsion, liposome, etc.

In certain embodiments, the disclosure relates to methods of preparing compounds disclosed herein comprising mixing one or more starting materials with reagents under conditions such that the products are formed.

DETAILED DISCUSSION

Figure 1:
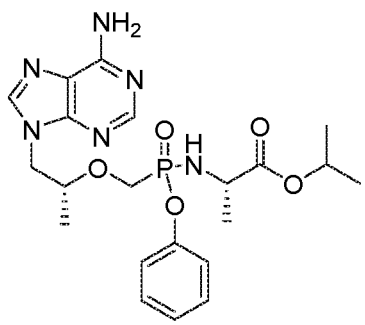
FIG. 1 illustrates known prodrug conjugates of tenofovir: Tenofovir-Alafenamide (TAF) and Hexadecyloxypropyl-Tenofovir (CMX-157) in the clinic and clinical trials pipeline.
Figure 1:
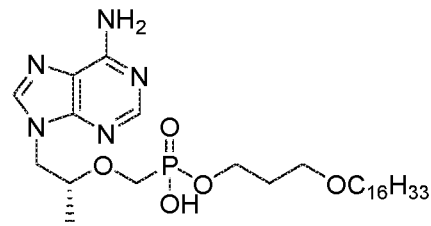
Figure 2:
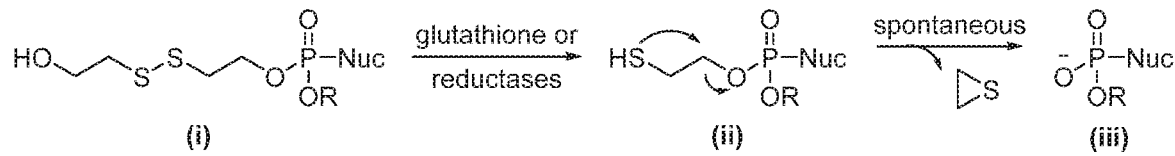
FIG. 2 illustrates a proposed mechanism for prodrug cleavage of dithioethanol (DTE) conjugates.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

To the extent that any chemical formulas reported herein contain one or more chiral centers, the formulas are intended to encompass all stable stereoisomers, enantiomers, and diastereomers. It is also understood that formula encompass all tautomeric forms.

It must be noted that, as used in the specification and the appended claims, the singular forms "a", "an", and "the" include plural referents unless the context clearly dictates otherwise.

"Subject" refers any animal, preferably a human patient, livestock, mouse model or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, a "lipid" group refers to a hydrophobic group that is naturally or non-naturally occurring that is an alkyl chain of greater than six carbons or highly insoluble in water. As used herein a lipid group is considered highly insoluble in water when the point of connection on the lipid group is replaced with a hydrogen and the resulting compound has a solubility of less than $0.63 \times 10^{-4}$% w/w (at 25° C.) in water, which is the percent solubility of octane in water by weight (see Solvent Recovery Handbook, 2nd Ed, Smallwood, 2002 by Blackwell Science, page 195). Examples of naturally occurring lipids include, but are not limited to, saturated or unsaturated hydrocarbon chains found in fatty acids, glycerolipids, cholesterol, steroids, polyketides, and derivatives. Non-limiting examples of non-naturally occurring lipids include, but are not limited to, derivatives of naturally occurring lipids, acrylic polymers, aromatic, and alkylated compounds and derivatives thereof as well as those described herein.

A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —CH$_2$—, —C(OH)$R_m$, —C(OH)(OH)—, —C(OH)H, —C(Hal)$R_m$—, —C(Hal)(Hal)-, —C(Hal)H—, —C(N$_3$)$R_m$—, —C(CN)$R_m$—, —C(CN)(CN)—, —C(CN)H—, —C(N$_3$)(N$_3$)—, —C(N$_3$)H—, —O—, —S—, —N—, —NH—, —N$R_m$—, —(C=O)—, —(C=NH)—, —(C=S)—, —(C=CH$_2$)—, which may contain single, double, or triple bonds individually and independently between the R groups. If an R is branched with an $R_m$ it may be terminated with a group such as —CH$_3$, —H, —CH=CH$_2$, —CCH, —OH, —SH, —NH$_2$, —N$_3$, —CN, or -Hal, NO$_2$, SO$_2$R or two branched Rs may form a cyclic structure. It is contemplated that in certain instances, the total Rs or "m" may be less than 100 or 50 or 25 or 10. Examples of linking groups include, but are not limited to, bridging alkyl groups, alkoxyalkyl groups and aminoalkyl groups.

As used herein, "alkyl" means a noncyclic straight chain or branched, unsaturated or saturated hydrocarbon such as those containing from 1 to 20 carbon atoms. A "higher alkyl" refers to unsaturated or saturated hydrocarbon having 6 or more carbon atoms. A "$C_8$-$C_{18}$" refers to an alkyl containing 8 to 18 carbon atoms. Likewise, a "$C_6$-$C_{22}$" refers to an alkyl containing 6 to 22 carbon atoms. Representative saturated straight chain alkyls include but are methyl, ethyl, n-propyl, n-butyl, n-pentyl, n-hexyl, n-septyl, n-octyl, n-nonyl, hexadecyl, dodecyl, tetradecyl, izosonyl, octadecyl, and the like; while saturated branched alkyls include, but are not limited to, isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include, but are not limited to, cyclopropyl, cyclobutyl, cyclopentyl, cyclohexyl, and the like; while unsaturated carbocycles include, but are not limited to, cyclopentenyl and cyclohexenyl, and the like. Carbocyclyls include, but are not limited to, cycloalkyls and cycloalkenyls.

"Heterocarbocycles" or "heterocarbocyclyl" groups are carbocycles which contain from 1 to 4 heteroatoms independently selected from nitrogen, phosphorous, oxygen and sulphur which may be saturated or unsaturated (but not aromatic), monocyclic or polycyclic, and wherein the nitrogen and sulphur heteroatoms may be optionally oxidized (e.g. —S(O)—, —SO$_2$—, —N(O)—), and the nitrogen heteroatom may be optionally quaternized. Heterocarbocycles include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 atoms such as phenyl, naphthyl and biphenyl.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkoxyalkyl" refers an alkyl group as defined above with the indicated number of carbon atoms attached through an alkyl bridge (i.e., —CH$_2$—O—CH$_2$CH$_3$).

"Alkylamino" refers an alkyl group as defined above with the indicated number of carbon atoms attached through an amino bridge. An example of an alkylamino is methylamino, (i.e., —NH—CH$_3$).

"Alkylthio" refers to an alkyl group as defined above with the indicated number of carbon atoms attached through a sulfur bridge. An example of an alkylthio is methylthio, (i.e., —S—CH$_3$).

"Alkanoyl" refers to an alkyl as defined above with the indicated number of carbon atoms attached through a carbonyl bride (i.e., —(C=O)alkyl).

The terms "cycloalkyl" and "cycloalkenyl" refer to mono-, bi-, or tri homocyclic ring groups of 3 to 15 carbon atoms which are, respectively, fully saturated and partially unsaturated.

The terms "halogen" or "Hal" refer to fluorine, chlorine, bromine, and iodine.

The term "substituted" refers to a molecule wherein at least one hydrogen atom is replaced with a substituent. When substituted, one or more of the groups are "substituents". The molecule may be multiply substituted. In the case of an oxo substituent (=O), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted", as used herein, means that substitution is optional and therefore it is possible for the designated atom to be unsubstituted.

The term "nucleoside" refers to a non-aromatic five membered ring substituted, e.g., tetrahydrofuran-2-yl substituted in the 5 position, with a nucleobase or heterocyclic derivative. The five membered ring and/or nucleobase may be further substituted or derivatized. Examples of nucleosides with modified adenosine or guanosine include, but are not limited to, hypoxanthine, xanthine, 7-methylguanine. Examples of nucleosides with modified cytidine, thymidine, or uridine include, but are not limited to, 5,6-dihydrouracil, 5-methylcytosine, 5-hydroxymethylcytosine.

A "nucleobase" refers to any variety of nitrogen containing monocyclic or bicyclic heterocycles. Nucleobases typically have at least one optionally substituted amino group connected to the ring(s), or a carbonyl/hydroxyl group within the ring(s), or an optionally substituted amide connected to the ring(s). It typically has two to four nitrogen atoms in the ring(s). Non-limiting examples of a nucleobase include adenine, guanine, cytosine, uracil, thymine, inosine, and heterocycles of the following structures:

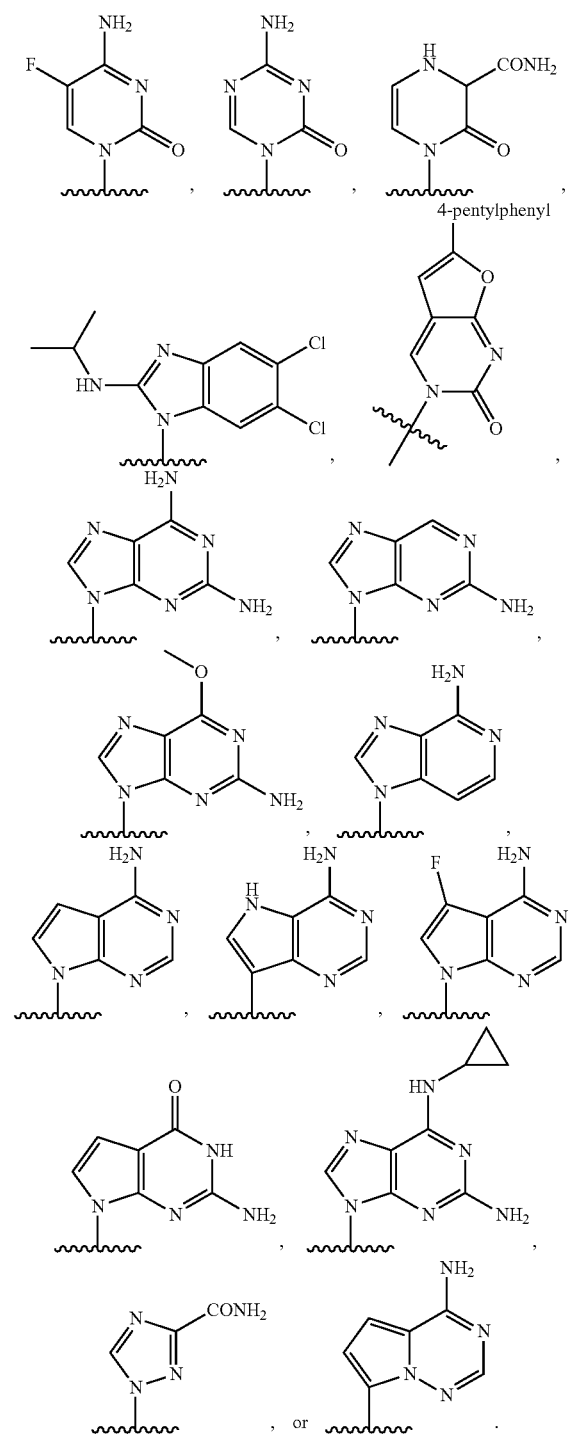

With regard to the nucleobases, it is contemplated that the term encompasses isobases. Contemplated isobases include 2'-deoxy-5-methylisocytidine (iC) and 2'-deoxy-isoguanosine (iG) (see U.S. Pat. Nos. 6,001,983; 6,037,120; 6,617, 106; and 6,977,161).

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, adding a hydroxyl group, replacing an oxygen atom with a sulfur atom, or replacing an amino group with a hydroxyl group, oxidizing a hydroxyl group to a carbonyl group, reducing a carbonyl group to a hydroxyl group, and reducing a carbon-to-carbon double bond to an alkyl group or oxidizing a carbon-to-carbon single bond to a double bond. A derivative optionally has one or more, the same or different, substitutions. Derivatives may be prepared by any variety of synthetic methods or appropriate adaptations presented in synthetic or organic chemistry text books, such as those provided in "March's Advanced Organic Chemistry: Reactions, Mechanisms, and Structure", Wiley, 6th Edition (2007) Michael B. Smith or "Domino Reactions in Organic Synthesis", Wiley (2006) Lutz F. Tietze, hereby incorporated by reference.

Lipid Disulfide Nucleotide Derivative

Disulfide-linked lipid conjugates were designed to test for penetration of the plasma membrane and release of the nucleoside within the target cell.

Figure 3:
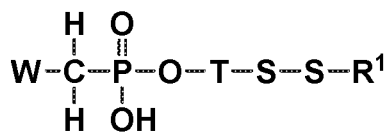
FIG. 3 illustrates some embodiments of this disclosure.
Figure 3:
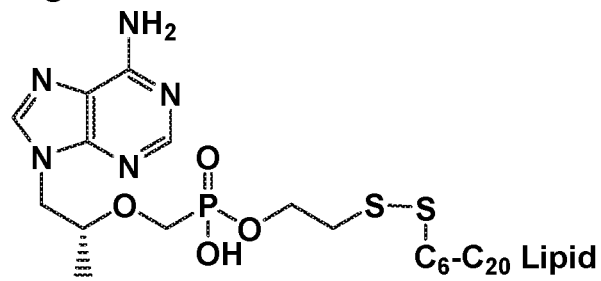

Glutathione, often referred to as GSH, is a tripeptide typically in millimolar concentrations (2-10 mM) within the cytosol that participates in a multitude of biological functions to promote detoxification of xenobiotics, mediates immunoregulation, and curbs oxidative stress, amongst others. GSH is seldom found in the extracellular space and thus creates a gradient that fosters intracellular reduction of disulfides and simultaneously promotes an oxidative environment to support S—S formation in the surrounding media. Reduction-sensitive lipid conjugates of tenofovir were developed (as shown in FIG. 3) that exhibit sub-nanomolar activity towards HIV-1 and are stable in human plasma for more than 24 h with a therapeutic index approaching 30,000.

In certain embodiments, a lipid disulfide nucleotide prodrug is a compound having Formula A,

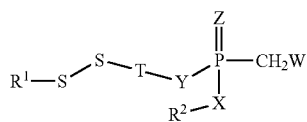

Formula A or pharmaceutically acceptable salts or derivatives thereof, wherein, T is a linking group;

W is a nucleoside or linking group for connecting to a nucleoside or nucleobase or, alkyl, alkenyl, alkynyl, alkanoyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein W is optionally substituted with one or more, the same or different, $R^{10}$; X and Y are individually and independently selected from O, S, NH or Se; Z is S, O or Se; $R^1$ is a lipid; $R^2$ is $R^1$SST-, hydrogen, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$, as described above, and wherein $R^{10}$ is optionally substituted with one or more, the same or different, $R^{11}$, as described above.

In certain embodiments, T is -Q-CH$_2$— and Q is —C$_6$H$_4$—, —(CH$_2$)$_n$—, —CH$_2$—C$_6$H$_4$—, a linking group providing an atomic chain of two, three or four atoms, —R$_m$—, wherein m is 1, 2, 3, or 4, or a bridging alkyl, alkenyl, carbocyclyl, optionally substituted carbocyclyl, heterocarbocyclyl, optionally substituted heterocarbocyclyl, aryl, optionally substituted aryl, heterocyclyl, or optionally substituted heterocyclyl.

In certain embodiments, a lipid disulfide derivative is a compound having the following Formula B,

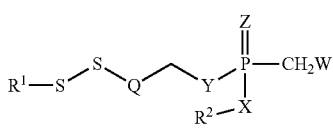

Formula B or salts or derivatives thereof wherein, Q is —C$_6$H$_4$—, —(CH$_2$)$_n$—, —CH$_2$—C$_6$H$_4$—, a linking group providing an atomic chain of two, three or four atoms, —R$_m$—, wherein m is 1, 2, 3, or 4, or a bridging alkyl, alkenyl, carbocyclyl, optimally substituted carbocyclyl, heterocarbocyclyl, optionally substituted heterocarbocyclyl, aryl, optionally substituted aryl, heterocyclyl, or optionally substituted heterocyclyl; n is 0, 1, 2, 3, 4, or 5; W is a nucleoside or linking group for connecting to a nucleoside or nucleobase or, alkyl, alkenyl, alkynyl, alkanoyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein W is optionally substituted with one or more, the same or different, $R^{10}$; X and Y are individually and independently selected from O, S, NH or Se; Z is S, O or Se; $R^1$ is a lipid; $R^2$ is $R^1$SSQCH$_2$-, hydrogen, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$, as described above, and wherein $R^{10}$ is optionally substituted with one or more, the same or different, $R^{11}$, as described above.

In certain embodiments, a lipid disulfide derivative is a compound having the following Formula C,

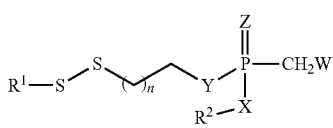

Formula C or salts or derivatives thereof wherein, n is 1, 2, 3, 4, or 5; W is a nucleoside or linking group for connecting to a nucleoside or nucleobase or, alkyl, alkenyl, alkynyl, alkanoyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein W is optionally substituted with one or more, the same or different, $R^{10}$; X and Y are individually and independently selected from O, S, NH or Se; Z is S, O or Se;

$R^1$ is a lipid; $R^2$ is $R^1$SS(CH$_2$)$_n$CH$_2$—, hydrogen, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$, as described above, and wherein $R^{10}$ is optionally substituted with one or more, the same or different, $R^{11}$, as described above.

In certain embodiments, $R^2$ is H, alkyl, or —$CH_2(CH_2)_nSSR^1$, more preferably, $R^2$ is H, methyl, or alkyl.

In certain embodiments, a lipid disulfide derivative is a compound having the following Formula D,

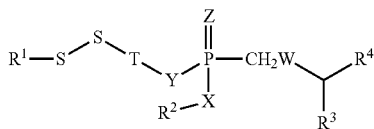

Formula D or salts or derivatives thereof wherein, T is a linking group or -QCH$_2$-; Q is —$C_6H_4$—, —$(CH_2)_n$—, —$CH_2$—$C_6H_4$—, a linking group providing an atomic chain of two, three or four atoms, —$R_m$—, wherein m is 1, 2, 3, or 4, or a bridging alkyl, alkenyl, carbocyclyl, optionally substituted carbocyclyl, heterocarbocyclyl, optionally substituted heterocarbocyclyl, aryl, optionally substituted aryl, heterocyclyl, or optionally substituted heterocyclyl; n is 1, 2, 3, 4, or 5; W is —$CH_2O$—, —$CH_2S$—, O, S, $CH_2NH$ or NH;

X is O, S, or NH; Y is O, S, or NH; Z is O, S or Se;

$R^1$ is a lipid, alkyl, ($C_8$-$C_{18}$)alkyl, ($C_6$-$C_{22}$)alkyl, higher alkyl, alkenyl, ($C_8$-$C_{18}$)alkenyl, ($C_6$-$C_{22}$)alkenyl, higher alkenyl, alkynyl, ($C_8$-$C_{18}$)alkynyl, ($C_6$-$C_{22}$)alkynyl, or higher alkynyl; or $R^1$ is aryl substituted with alkyl, ($C_8$-$C_{18}$)alkyl, ($C_6$-$C_{22}$)alkyl, higher alkyl, alkenyl, ($C_8$-$C_{18}$)alkenyl, ($C_6$-$C_{22}$)alkenyl, higher alkenyl, alkynyl, ($C_8$-$C_{18}$)alkynyl, ($C_6$-$C_{22}$)alkynyl, or higher alkynyl wherein $R^1$ is optionally substituted with one or more, the same or different, $R^{10}$; $R^2$ is $R^1$SST-, hydrogen, methyl, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$; $R^3$ is nucleotide, alkyl, alkoxyalkyl, carbocyclyl, or heterocarbocyclyl substituted with a nucleobase or a heterocyclyl, wherein $R^3$ is optionally substituted with one or more, the same or different, $R^{10}$; or $R^3$ is tetrahydrofuran-2-yl or cyclopentenyl, substituted with a nucleobase or a heterocyclyl, wherein $R^3$ is optionally further substituted with one or more, the same or different, $R^{10}$, wherein the optional further substitution is on the nucleotide, alkyl, alkoxyalkyl, nucleobase, carbocyclyl, cyclopentenyl, heterocarbocyclyl, tetrahydrofuran-2-yl, or heterocyclyl; $R^4$ is hydrogen, alkyl, halogen, or hydroxymethyl, wherein $R^4$ is optionally substituted with one or more, the same or different, $R^{10}$; or $R^2$ and $R^4$ and attached atoms come together to form a six membered heterocyclyl; or $R^3$ and $R^4$ and attached atoms come together to form a five membered carbocyclic or heterocarbocyclic ring substituted with a nucleobase or a heterocyclyl which is optionally further substituted with one or more, the same or different, $R^{10}$, wherein the optional further substitution is on the five membered carbocyclic or heterocarbocyclic ring, nucleobase, or heterocyclyl; $R^{10}$ is as described above, and may be optionally substituted with one or more, the same or different, $R^{11}$, as described above.

In certain embodiments, $R^2X$ is HO—, $R^1$SSTO—, methylO—, or alkylO—.

In certain embodiments, X and Y are O.
In certain embodiments, X and Y and Z are O.
In certain embodiments, X is NH and Y and Z are O.
In certain embodiments, W is —O—.

In certain embodiments, W is —O—, and $R^2X$ is HO—, $R^1$SSTO—, methyl-, or alkylO—.

In certain embodiments, W is —O—, and X and Y are O.
In certain embodiments, W is —O—, and X and Y and Z are O.
In certain embodiments, W is —O—, and X is NH and Y and Z are O, and $R^2$ is H, $R^1$SSTO—, methyl-, or alkyl-.
In certain embodiments, W is O, and $R^2X$ is HO—, $R^1$SSTO—, methylO—, or alkylO—.
In certain embodiments, W is O, and X and Y are O, and $R^2X$ is HO—, $R^1$SSTO—, methylO—, or alkylO—.
In certain embodiments, W is O, and X and Y and Z are O, and $R^2X$ is HO—, $R^1$SSTO—, methylO—, or alkylO—.
In certain embodiments, W is O, and X is NH and Y and Z are O, and $R^2$ is H, $R^1$SSTO—, methyl-, or alkyl-.

In certain embodiments, a lipid disulfide derivative is a compound having the following Formula E,

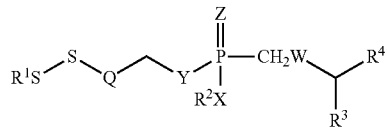

Formula E or salts or derivatives thereof wherein, Q is —$C_6H_4$—, —$(CH_2)_n$—, —$CH_2$—$C_6H_4$—, a linking group providing an atomic chain of two, three or four atoms, —$R_m$—, wherein m is 1, 2, 3, 4 or 5, or a bridging alkyl, alkenyl, carbocyclyl, optionally substituted carbocyclyl, heterocarbocyclyl, optionally substituted heterocarbocyclyl, aryl, optionally substituted aryl, heterocyclyl, or optionally substituted heterocyclyl; n is 1, 2, 3, 4, or 5; W is —$CH_2O$—, —$CH_2S$—, O, or S; X is O, S, or NH; Y is O, S, or NH; Z is O or S; $R^1$ is a lipid, alkyl, ($C_8$-$C_{18}$)alkyl, ($C_6$-$C_{22}$)alkyl, higher alkyl, alkenyl, ($C_8$-$C_{18}$)alkenyl, ($C_6$-$C_{22}$)alkenyl, higher alkenyl, alkynyl, ($C_8$-$C_{18}$)alkynyl, ($C_6$-$C_{22}$)alkynyl, or higher alkynyl; or $R^1$ is aryl substituted with alkyl, ($C_8$-$C_{18}$)alkyl, ($C_6$-$C_{22}$)alkyl, higher alkyl, alkenyl, ($C_8$-$C_{18}$)alkenyl, ($C_6$-$C_{22}$)alkenyl, higher alkenyl, alkynyl, ($C_8$-$C_{18}$)alkynyl, ($C_6$-$C_{22}$)alkynyl, or higher alkynyl wherein $R^1$ is optionally substituted with one or more, the same or different, $R^{10}$; $R^2$ is $R^1$SSQCH$_2$-, hydrogen, methyl, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$; $R^3$ is nucleotide, alkyl, alkoxyalkyl, carbocyclyl, or heterocarbocyclyl substituted with a nucleobase or a heterocyclyl, wherein $R^3$ is optionally substituted with one or more, the same or different, $R^{10}$; or $R^3$ is tetrahydrofuran-2-yl or cyclopentenyl, substituted with a nucleobase or a heterocyclyl, wherein $R^3$ is optionally further substituted with one or more, the same or different, $R^{10}$, wherein the optional further substitution is on the nucleotide, alkyl, alkoxyalkyl, nucleobase, carbocyclyl, cyclopentenyl, heterocarbocyclyl, tetrahydrofuran-2-yl, or heterocyclyl; $R^4$ is hydrogen, alkyl, halogen, or hydroxymethyl, wherein $R^4$ is optionally substituted with one or more, the same or different, $R^{10}$; or $R^2$ and $R^4$ and attached atoms come together to form a six membered heterocyclyl; or $R^3$ and $R^4$ and attached atoms come together to form a five membered carbocyclic or heterocarbocyclic ring substituted with a nucleobase or a heterocyclyl which is optionally further substituted with one or more, the same or different, $R^{10}$, wherein the optional further substitution is on the five membered carbocyclic or heterocarbocyclic ring, nucleobase, or heterocyclyl; $R^{10}$ is as described above, and may be optionally substituted with one or more, the same or different, $R^{11}$, as described above.

In certain embodiments, $R^2X$ is HO—, $R^1SSQCH_2O$—, methylO—, or alkylO—.

In certain embodiments, X and Y are O.

In certain embodiments, X and Y and Z are O.

In certain embodiments, X is NH and Y and Z are O.

In certain embodiments, W is —O—.

In certain embodiments, W is —O—, and $R^2X$ is HO—, $R^1SSQCH_2O$—, methyl-, or alkylO—.

In certain embodiments, W is —O—, and X and Y are O.

In certain embodiments, W is —O—, and X and Y and Z are O.

In certain embodiments, W is —O—, and X is NH and Y and Z are O, and $R^2$ is H, $R^1SSQCH_2O$—, methyl-, or alkyl-.

In certain embodiments, W is O, and $R^2X$ is HO—, $R^1SSQCH_2O$—, methylO—, or alkylO—.

In certain embodiments, W is O, and X and Y are O, and $R^2X$ is HO—, $R^1SSQCH_2O$—, methylO—, or alkylO—.

In certain embodiments, W is O, and X and Y and Z are O, and $R^2X$ is HO—, $R^1SSQCH_2O$—, methylO—, or alkylO—.

In certain embodiments, W is O, and X is NH and Y and Z are O, and $R^2$ is H, $R^1SSQCH_2O$—, methyl-, or alkyl-.

In certain embodiments, a lipid disulfide derivative is a compound having the following Formula F, Formula F or salts or derivatives thereof wherein, n is 1, 2, 3, 4, or 5; W is —$CH_2O$—, —$CH_2S$—, O, or S; X is O, S, or NH; Y is O, S, or NH; Z is O or S; $R^1$ is a lipid, alkyl, $(C_8$-$C_{18})$alkyl, $(C_6$-$C_{22})$alkyl, higher alkyl, alkenyl, $(C_8$-$C_{18})$alkenyl, $(C_6$-$C_{22})$alkenyl, higher alkenyl, alkynyl, $(C_8$-$C_{18})$alkynyl, $(C_6$-$C_{22})$alkynyl, or higher alkynyl; or $R^1$ is aryl substituted with alkyl, $(C_8$-$C_{18})$alkyl, $(C_6$-$C_{22})$alkyl, higher alkyl, alkenyl, $(C_8$-$C_{18})$alkenyl, $(C_6$-$C_{22})$alkenyl, higher alkenyl, alkynyl, $(C_8$-$C_{18})$alkynyl, $(C_6$-$C_{22})$alkynyl, or higher alkynyl wherein $R^1$ is optionally substituted with one or more, the same or different, $R^{10}$; $R^2$ is $R^1SS(CH_2)_nCH_2$—, hydrogen, methyl, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$; $R^3$ is nucleotide, alkyl, alkoxyalkyl, carbocyclyl, or heterocarbocyclyl substituted with a nucleobase or a heterocyclyl, wherein $R^3$ is optionally substituted with one or more, the same or different, $R^{10}$; or $R^3$ is tetrahydrofuran-2-yl or cyclopentenyl, substituted with a nucleobase or a heterocyclyl, wherein $R^3$ is optionally further substituted with one or more, the same or different, $R^{10}$, wherein the optional further substitution is on the nucleotide, alkyl, alkoxyalkyl, nucleobase, carbocyclyl, cyclopentenyl, heterocarbocyclyl, tetrahydrofuran-2-yl, or heterocyclyl; $R^4$ is hydrogen, alkyl, halogen, or hydroxymethyl, wherein $R^4$ is optionally substituted with one or more, the same or different, $R^{10}$; or $R^2$ and $R^4$ and attached atoms come together to form a six membered heterocyclyl; or $R^3$ and $R^4$ and attached atoms come together to form a five membered carbocyclic or heterocarbocyclic ring substituted with a nucleobase or a heterocyclyl which is optionally further substituted with one or more, the same or different, $R^{10}$, wherein the optional further substitution is on the five membered carbocyclic or heterocarbocyclic ring, nucleobase, or heterocyclyl; $R^{10}$ is as described above, and wherein $R^{10}$ is optionally substituted with one or more, the same or different, $R^{11}$, as described above.

In certain embodiments, $R^2X$ is HO—, $R^1SS(CH_2)_nCH_2O$—, methylO—, or alkylO—.

In certain embodiments, X and Y are O.

In certain embodiments, X and Y and Z are O.

In certain embodiments, X is NH and Y and Z are O.

In certain embodiments, W is —$CH_2O$—.

In certain embodiments, W is —$CH_2O$—, and $R^2X$ is HO—, $R^1SS(CH_2)_nCH_2O$—, methyl-, or alkylO—.

In certain embodiments, W is —$CH_2O$—, and X and Y are O.

In certain embodiments, W is —$CH_2O$—, and X and Y and Z are O.

In certain embodiments, W is —$CH_2O$—, and X is NH and Y and Z are O, and $R^2$ is H, $R^1SS(CH_2)_nCH_2O$—, methyl-, or alkyl-.

In certain embodiments, W is O.

In certain embodiments, W is O, and $R^2X$ is HO—, $R^1SS(CH_2)_nCH_2O$—, methylO—, or alkylO—.

In certain embodiments, W is O, and X and Y are O, and $R^2X$ is HO—, $R^1SS(CH_2)_nCH_2O$—, methylO—, or alkylO—.

In certain embodiments, W is O, and X and Y and Z are O, and $R^2X$ is HO—, $R^1SS(CH_2)_nCH_2O$—, methylO—, or alkylO—.

In certain embodiments, W is O, and X is NH and Y and Z are O, and $R^2$ is H, $R^1SS(CH_2)_nCH_2O$—, methyl-, or alkyl-.

In certain embodiments, a lipid disulfide derivative is a compound having the following Formula, Formula IA Formula IF Formula IL Formula IQ Formula IV
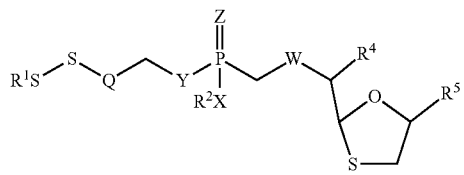

Formula II
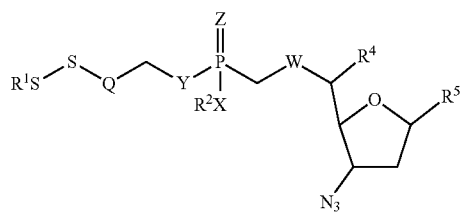

Formula IIE
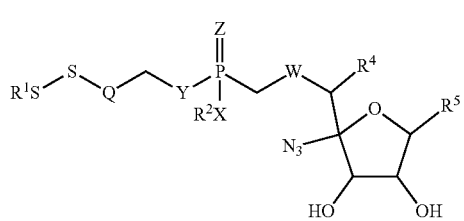

Formula IIK
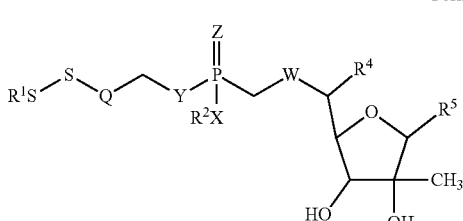

Formula IIP
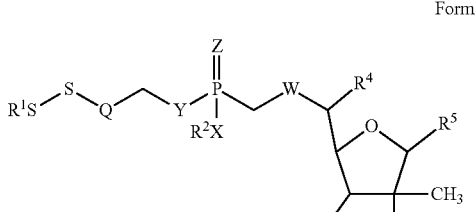

Formula IIU
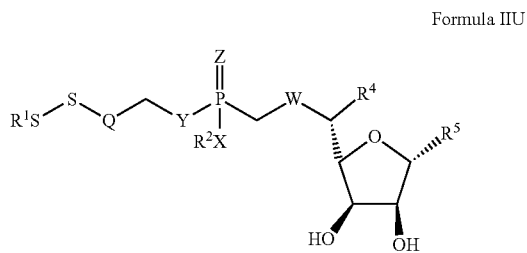

Formula IIW
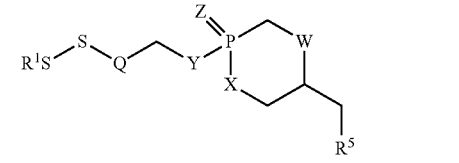

Formula IIIA
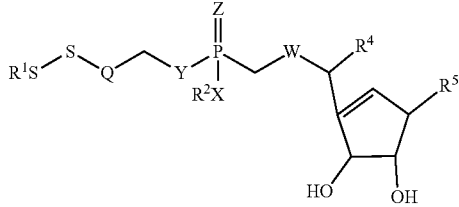

Formula IIIF
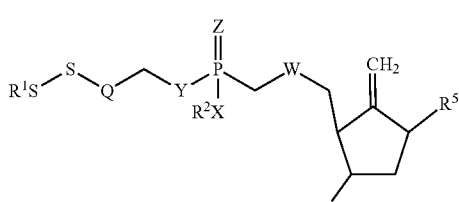

Formula IIIL
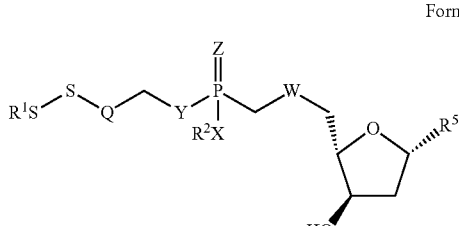

Formula IIIQ
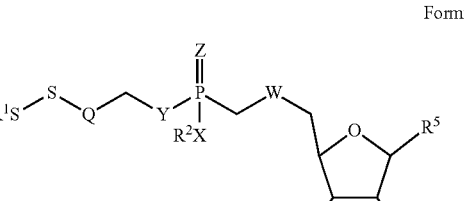

Formula IIIV or salts or derivatives thereof wherein, Q is —$C_6H_4$—, —$(CH_2)_n$—, —$CH_2$—$C_6H_4$—, a linking group providing an atomic chain of two, three or four atoms, —$R_m$—, wherein m is 1, 2, 3, or 4, or a bridging alkyl, alkenyl, carbocyclyl, optionally substituted carbocyclyl, heterocarbocyclyl, optionally substituted heterocarbocyclyl, aryl, optionally substituted aryl, heterocyclyl, or optionally substituted heterocyclyl; n is 1, 2, 3, 4, or 5; W is —$CH_2O$—, —$CH_2S$—, O, or S; X is O, S, or NH; Y is O, S, or NH; Z is O or S; $R^1$ is a lipid, alkyl, ($C_8$-$C_{18}$)alkyl, ($C_6$-$C_{22}$)alkyl, higher alkyl, alkenyl, ($C_8$-$C_{18}$)alkenyl, ($C_6$-$C_{22}$)alkenyl, higher alkenyl, alkynyl, ($C_8$-$C_{18}$)alkynyl, ($C_6$-$C_{22}$)alkynyl, or higher alkynyl; or $R^1$ is aryl substituted with alkyl, ($C_8$-$C_{18}$)alkyl, ($C_6$-$C_{22}$)alkyl, higher alkyl, alkenyl, ($C_8$-$C_{18}$)alkenyl, ($C_6$-$C_{22}$)alkenyl, higher alkenyl, alkynyl, ($C_8$-$C_{18}$)alkynyl, ($C_6$-$C_{22}$)alkynyl, or higher alkynyl wherein $R^1$ is optionally substituted with one or more, the same or different, $R^{10}$; $R^2$ is $R^1SSQCH_2$—, hydrogen, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$; $R^5$ is a nucleobase or a heterocyclyl, wherein $R^5$ is optionally substituted with one or more, the same or different, $R^{10}$; $R^4$ is hydrogen, alkyl, halogen, or hydroxymethyl, wherein $R^4$ is optionally substituted with one or more, the same or different, $R^{10}$; $R^{10}$ is as described above, and wherein $R^{10}$ is optionally substituted with one or more, the same or different, $R^{11}$, as described above.

In certain embodiments, a lipid dithiol phosphodiester nucleotide derivative is a compound having the following Formula, Formula IB

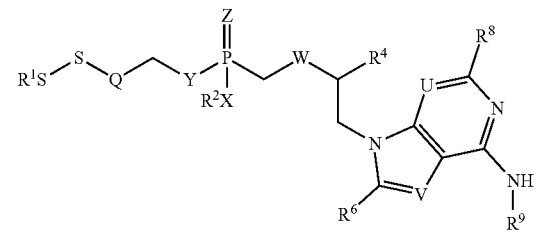

Formula IC

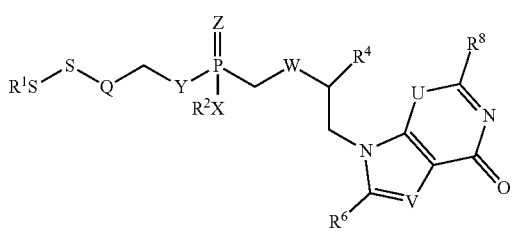

Formula ID

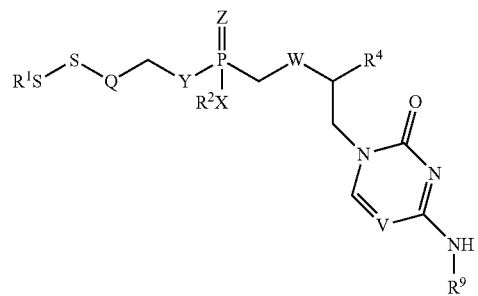

Formula IE

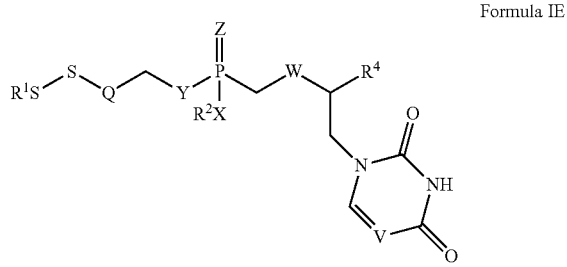

-continued

Formula IG

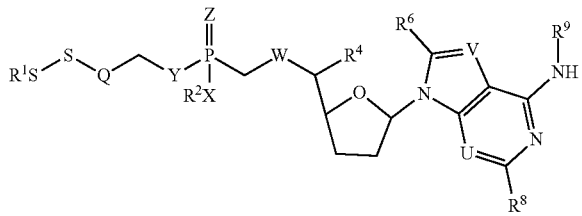

Formula IH

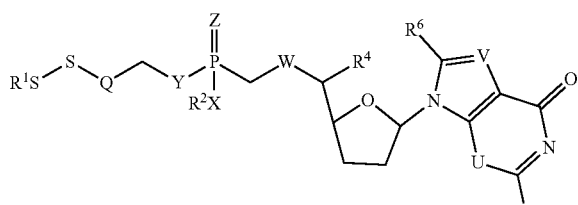

Formula IJ

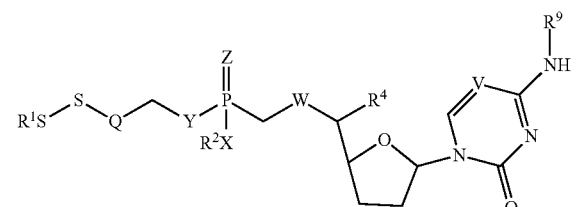

Formula IK

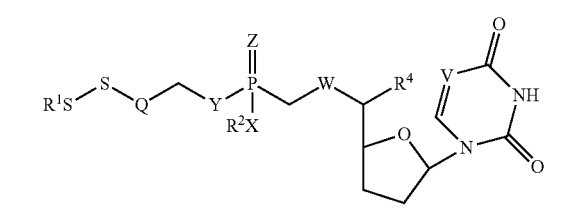

Formula IM

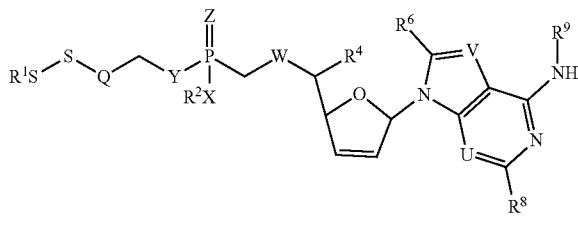

Formula IN

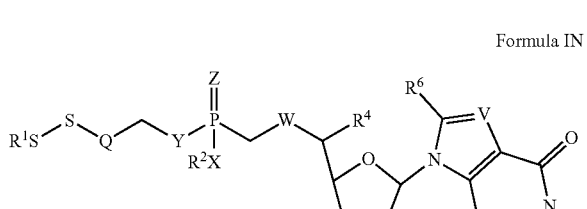

Formula IO
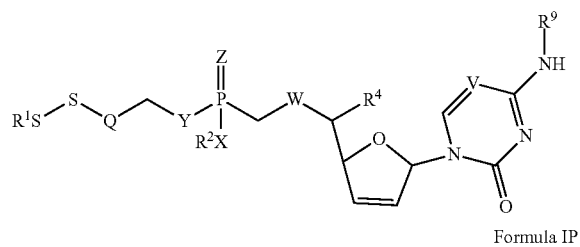
Formula IP
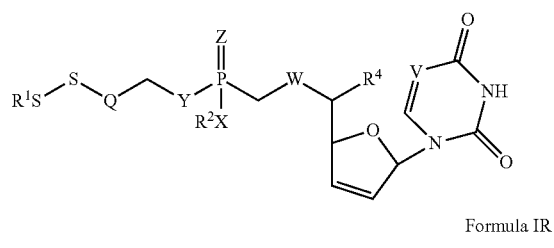
Formula IR
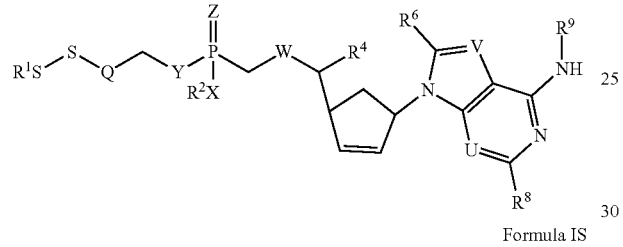
Formula IS
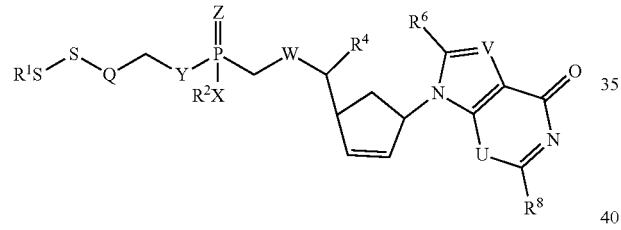
Formula IT
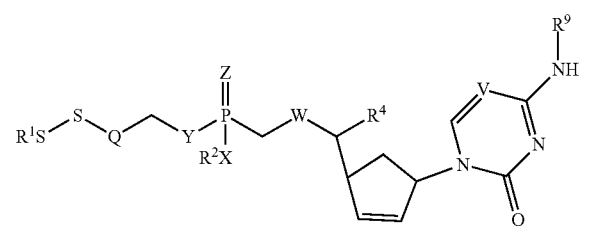
Formula IU
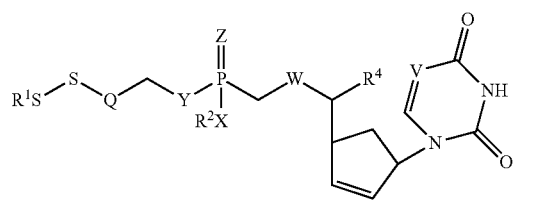
Formula IW
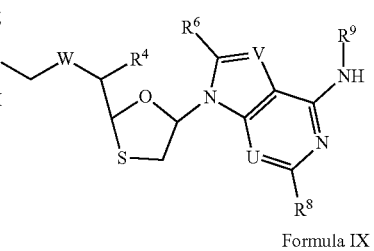
Formula IX
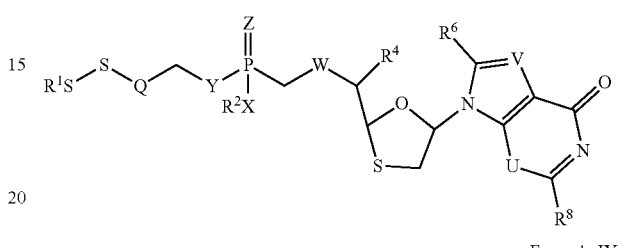
Formula IY
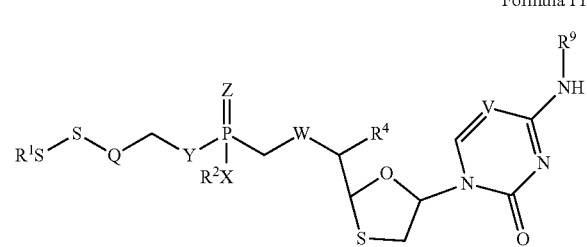
Formula IZ
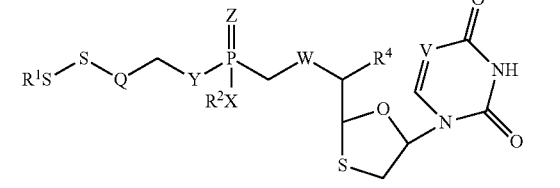
Formula IIA
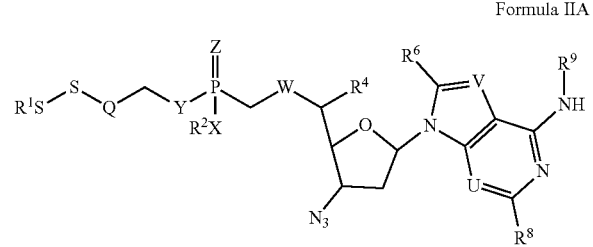
Formula IIB
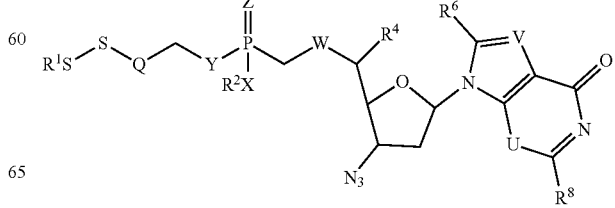

Formula IIC
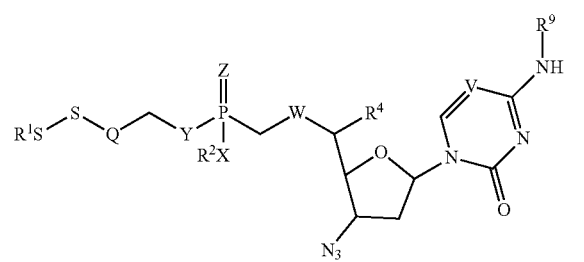
Formula IID
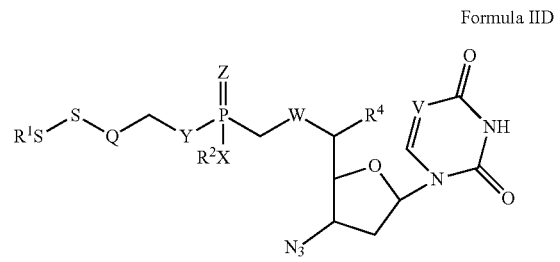
Formula IIF
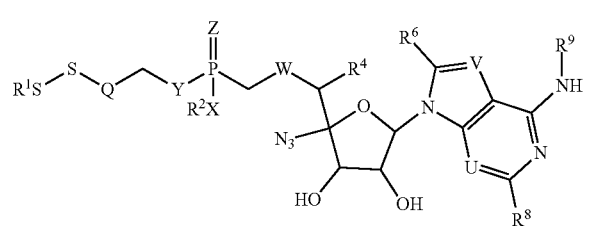
Formula IIG
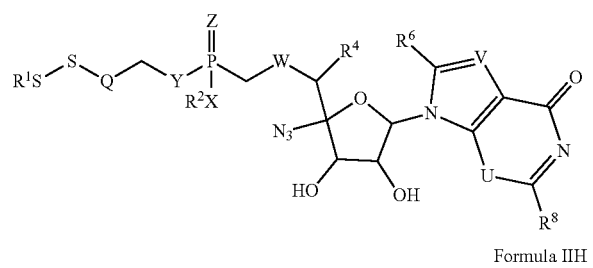
Formula IIH
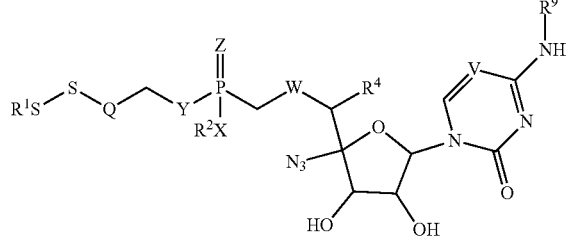
Formula IIJ
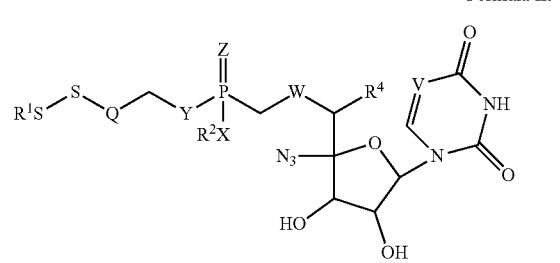
Formula IIL
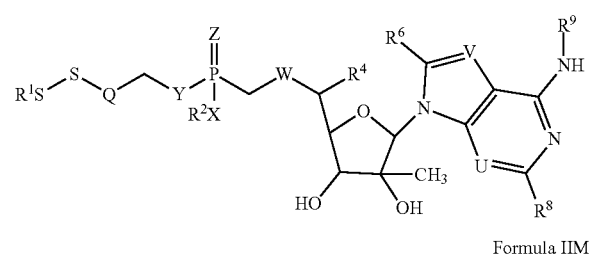
Formula IIM
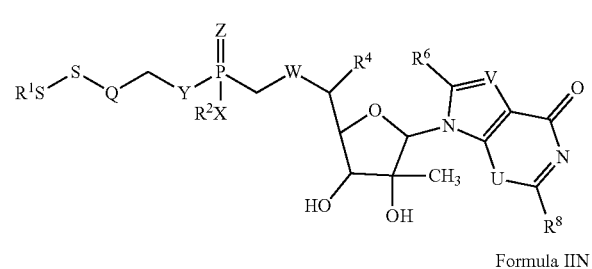
Formula IIN
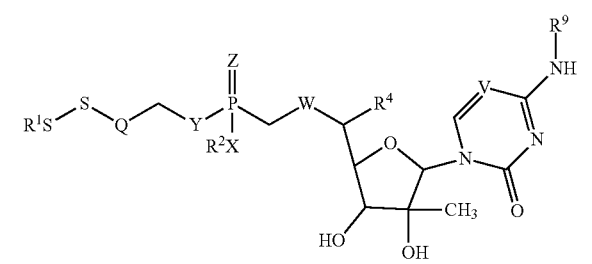
Formula IIO
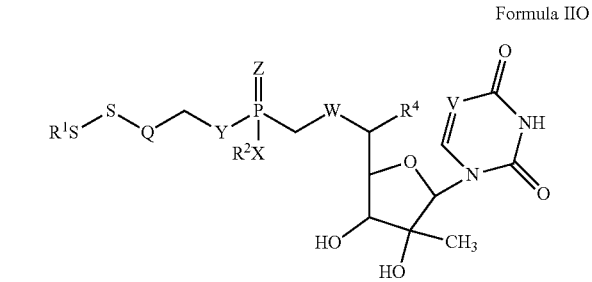
Formula IIQ
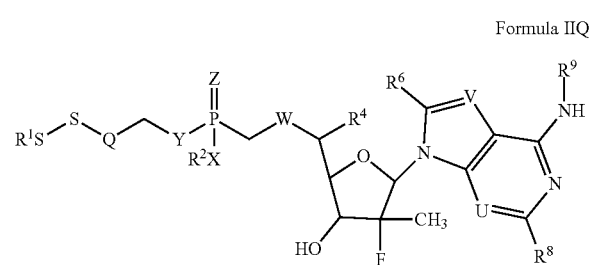
Formula IIR Formula IIS
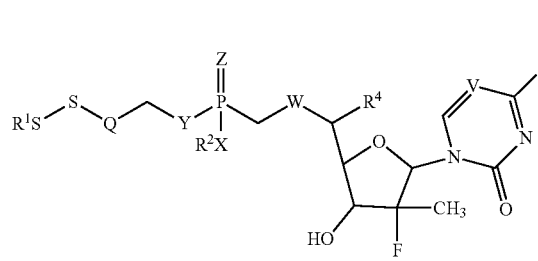
Formula IIT
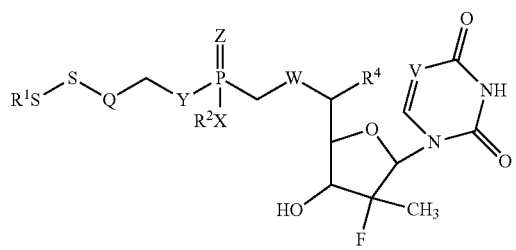
Formula IV
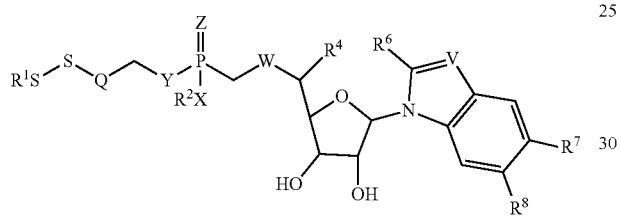
Formula IX
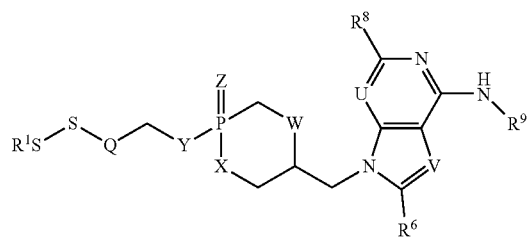
Formula IY
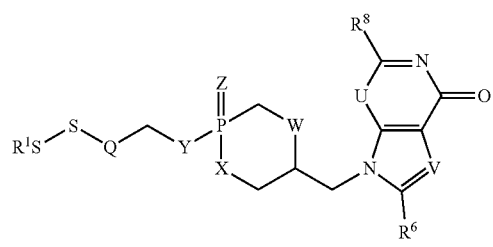
Formula IZ
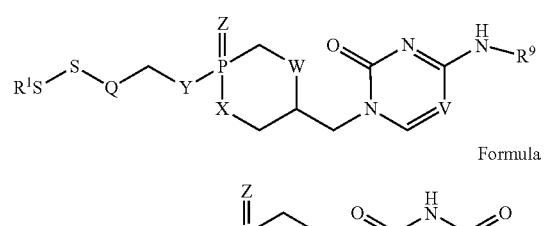
Formula III
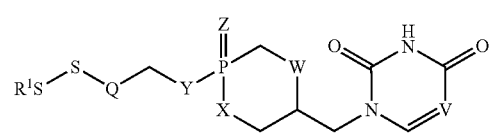
Formula IIIB
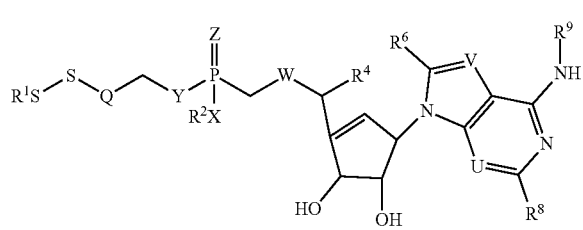
Formula IIIC
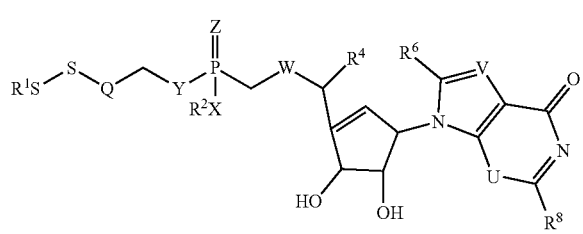
Formula IIID
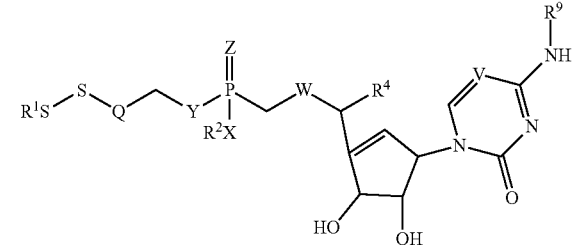
Formula IIIE
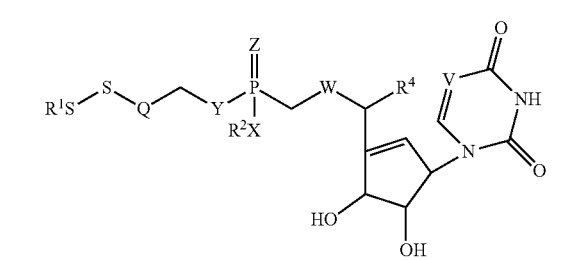
Formula IIIG
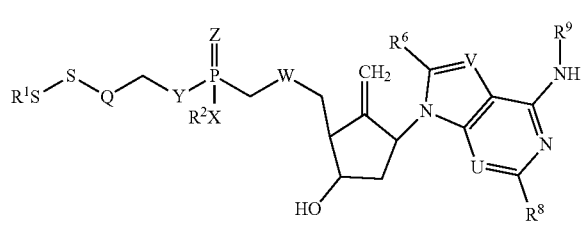
Formula IIIH Formula IIIJ
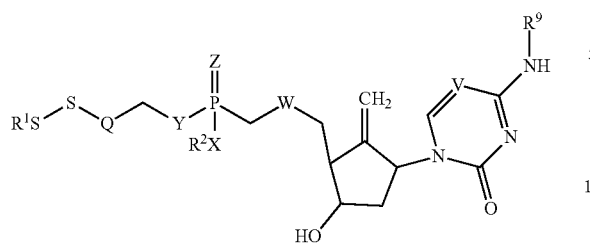
Formula IIIK
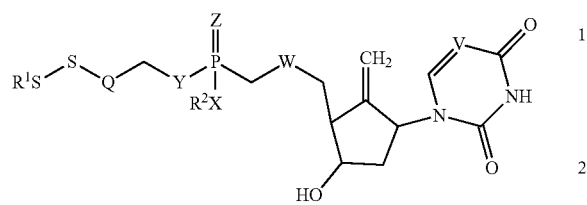
Formula IIIM
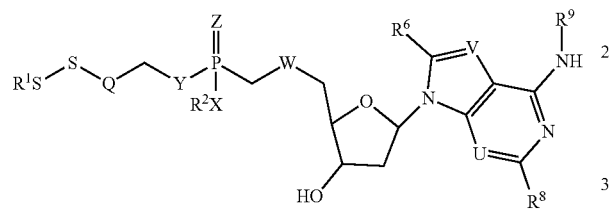
Formula IIIN
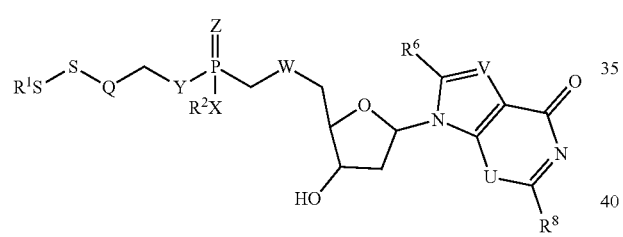
Formula IIIO
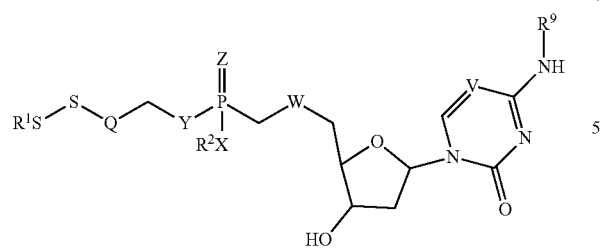
Formula IIIP
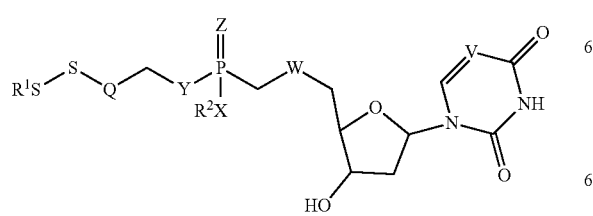
Formula IIIR
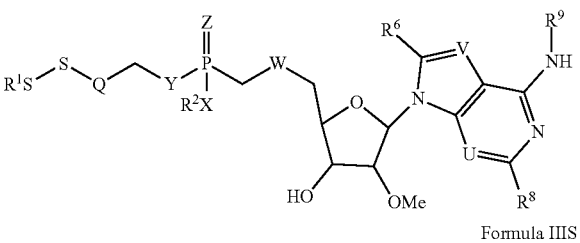
Formula IIIS
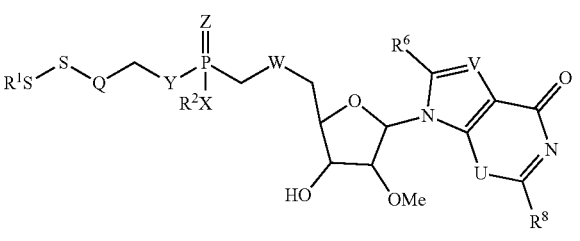
Formula IIIT
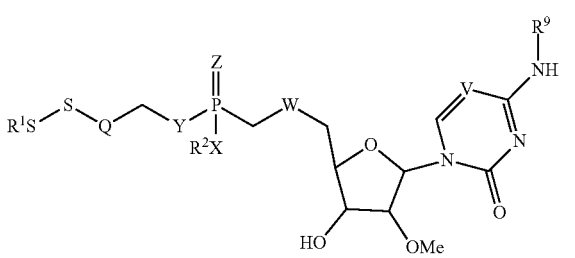
Formula IIIU
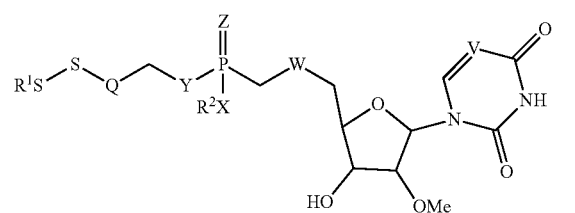
Formula IIIW
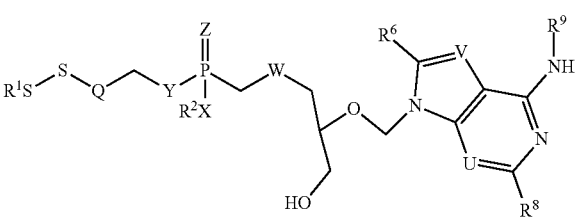
Formula IIIX
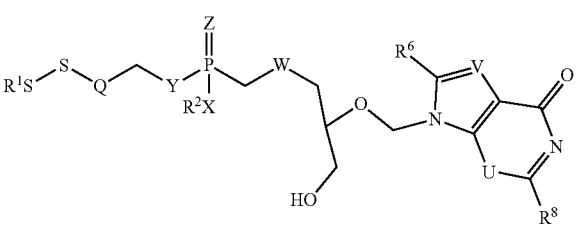

-continued

Formula IIIY

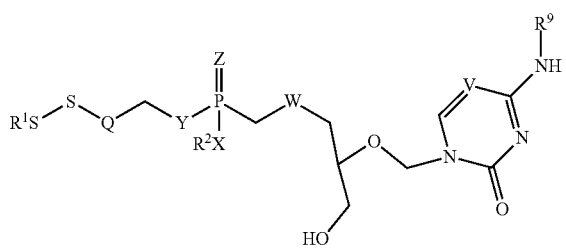

Formula IIIZ

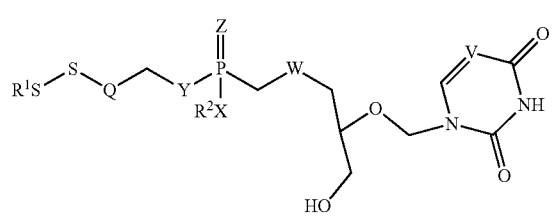

or salts or derivatives thereof wherein, Q is —C$_6$H$_4$—, —(CH$_2$)$_n$—, —CH$_2$—C$_6$H$_4$—, a linking group providing an atomic chain of two, three or four atoms, —R$_m$—, wherein m is 1, 2, 3, 4, or 5, or a bridging alkyl, alkenyl, carbocyclyl, substituted carbocyclyl, heterocarbocyclyl, substituted heterocarbocyclyl, aryl, substituted aryl, heterocyclyl, or substituted heterocyclyl; n is 1, 2, 3, 4, or 5; U is N or CH; V is N or CR$^7$; W is O or S; X is O, S, NH or Se; Y is O, S, NH or Se; Z is O, S or Se; R$^1$ is a lipid, alkyl, (C$_8$-C$_{18}$)alkyl, (C$_6$-C$_{22}$)alkyl, higher alkyl, alkenyl, (C$_8$-C$_{18}$)alkenyl, (C$_6$-C$_{22}$)alkenyl, higher alkenyl, alkynyl, (C$_8$-C$_{18}$)alkynyl, (C$_6$-C$_{22}$)alkynyl, or higher alkynyl; or R$^1$ is aryl substituted with alkyl, (C$_8$-C$_{18}$)alkyl, (C$_6$-C$_{22}$)alkyl, higher alkyl, alkenyl, (C$_8$-C$_{18}$)alkenyl, (C$_6$-C$_{22}$)alkenyl, higher alkenyl, alkynyl, (C$_8$-C$_{18}$)alkynyl, (C$_6$-C$_{22}$)alkynyl, or higher alkynyl wherein R$^1$ is optionally substituted with one or more, the same or different, R$^{10}$; R$^2$ is R$^1$SSQCH$_2$—, hydrogen, alkyl, aryl, phenyl, 4-fluorophenyl, 4-chlorophenyl, 4-bromophenyl, naphthyl, or heterocyclyl, wherein R$^2$ is optionally substituted with one or more, the same or different, R$^{10}$; R$^4$ is hydrogen, alkyl, halogen, or hydroxymethyl, wherein R$^4$ is optionally substituted with one or more, the same or different, R$^{10}$; R$^6$ is hydrogen, alkyl, amino, or halogen, wherein R$^6$ is optionally substituted with one or more, the same or different, R$^{10}$; R$^7$ is hydrogen, alkyl, or halogen, wherein R$^7$ is optionally substituted with one or more, the same or different, R$^{10}$; R$^8$ is hydrogen, alkyl, amino, or halogen, wherein R$^8$ is optionally substituted with one or more, the same or different, R$^{10}$; R$^9$ is hydrogen, alkyl, cyclopropyl, or carbocyclyl, wherein R$^9$ is optionally substituted with one or more, the same or different, R$^{10}$; R$^{10}$ is as described above, and wherein R$^{10}$ is optionally substituted with one or more, the same or different, R$^{11}$, as described above.

Exemplary compounds include:

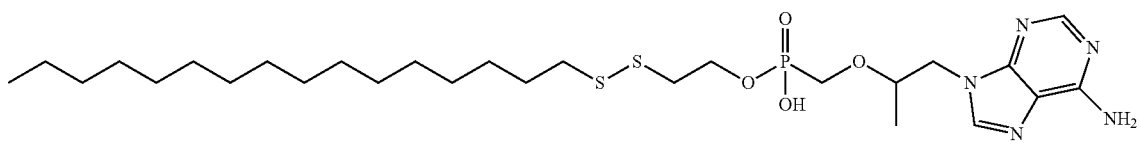 [SMILES: CCCCCCCCCCCCCCCCSSCCOP(=O)(O)COC(C)Cn1cnc2c(N)ncnc21]

2-((hexadecyldisulfanyl)methyl)benzyl hydrogen (((1-(6-amino-9H-purin-9-yl)propan-2-yl)oxy)methyl)phosphonate or salts thereof;

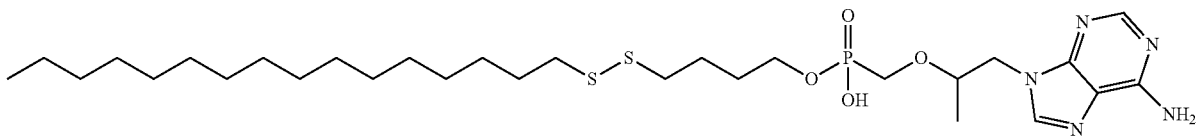 [SMILES: CCCCCCCCCCCCCCCCSSCCCCOP(=O)(O)COC(C)Cn1cnc2c(N)ncnc21]

4-(hexadecyldisulfanyl)butyl hydrogen (((1-(6-amino-9H-purin-9-yl)propan-2-yl)oxy)methyl)phosphonate or salts thereof;

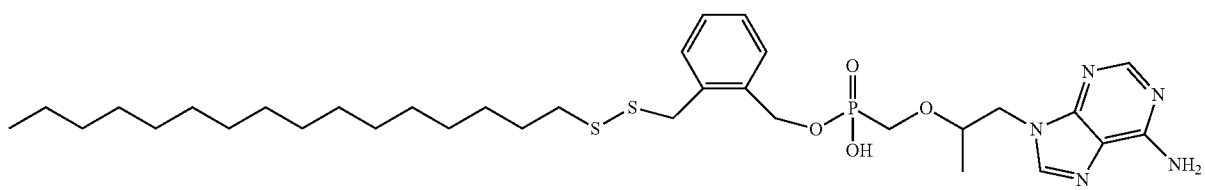 [SMILES: CCCCCCCCCCCCCCCCSSCc1ccccc1COP(=O)(O)COC(C)Cn1cnc2c(N)ncnc21]

2-((hexadecyldisulfanyl)methyl)benzyl hydrogen (((1-(6-amino-9H-purin-9-yl)propan-2-yl)oxy)methyl)phosphonate or salts thereof:

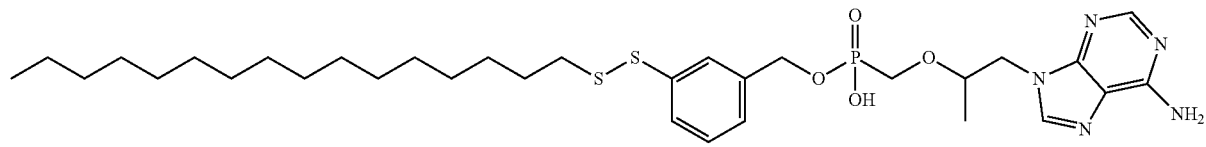 [SMILES: CCCCCCCCCCCCCCCCSSc1cccc(COP(=O)(O)COC(C)Cn2cnc3c(N)ncnc32)c1]

3-(hexadecyldisulfanyl)benzyl hydrogen (((1-(6-amino-9H-purin-9-yl)propan-2-yl)oxy)methyl)phosphonate or salts thereof;

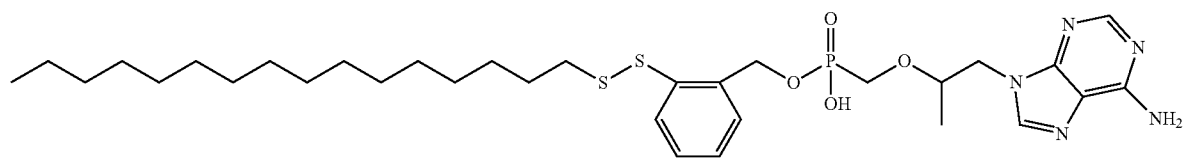 [SMILES: CCCCCCCCCCCCCCCCSSc1ccccc1COP(=O)(O)COC(C)Cn1cnc2c(N)ncnc21]

2-(hexadecyldisulfanyl)benzyl hydrogen (((1-(6-amino-9H-purin-9-yl)propan-2-yl)oxy)methyl)phosphonate or salts thereof;

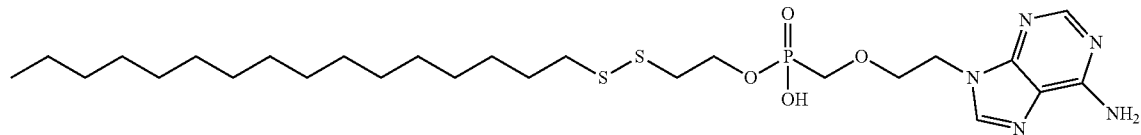 [SMILES: CCCCCCCCCCCCCCCCSSCCOP(=O)(O)COCCn1cnc2c(N)ncnc21]

2-(hexadecyldisulfanyl)ethyl hydrogen ((2-(6-amino-9H-purin-9-yl)ethoxy)methyl)phosphonate or salts thereof;

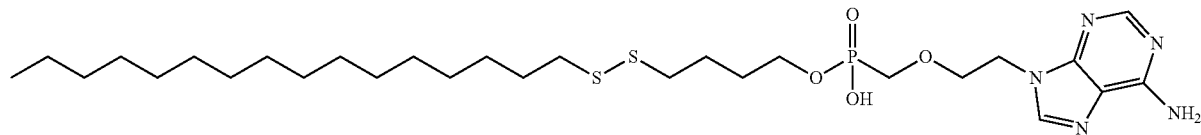 [SMILES: CCCCCCCCCCCCCCCCSSCCCCOP(=O)(O)COCCn1cnc2c(N)ncnc21]

4-(hexadecyldisulfanyl)butyl hydrogen ((2-(6-amino-9H-purin-9-yl)ethoxy)methyl)phosphonate or salts thereof;

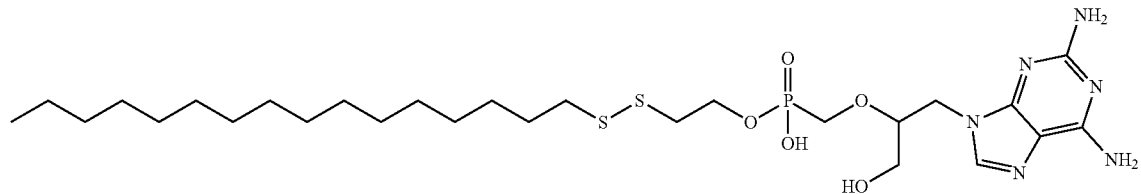 [SMILES: CCCCCCCCCCCCCCCCSSCCOP(=O)(O)COC(CO)Cn1cnc2c(N)nc(N)nc21]

2-(hexadecyldisulfanyl)ethyl hydrogen (((1-(2,6-diamino-9H-purin-9-yl)-3-hydroxypropan-2-yl)oxy)methyl)phosphonate or salts thereof;

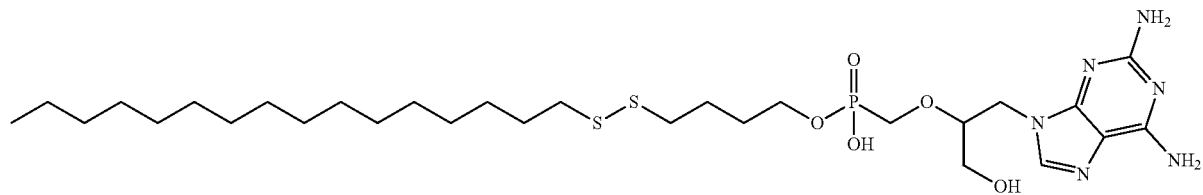 [SMILES: CCCCCCCCCCCCCCCCSSCCCCOP(=O)(O)COC(CO)Cn1cnc2c(N)nc(N)nc21]

4-(hexadecyldisulfanyl)butyl hydrogen (((1-(2,6-diamino-9H-purin-9-yl)-3-hydroxypropan-2-yl)oxy)methyl)phosphonate or salts thereof;

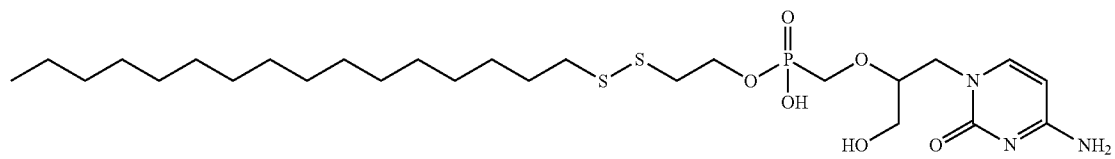 [SMILES: CCCCCCCCCCCCCCCCSSCCOP(=O)(O)COC(CO)Cn1ccc(N)nc1=O]

2-(hexadecyldisulfanyl)ethyl hydrogen (((1-(4-amino-2-oxopyrimidin-1(2H)-yl)-3-hydroxypropan-2-yl)oxy)methyl) phosphonate or salts thereof;

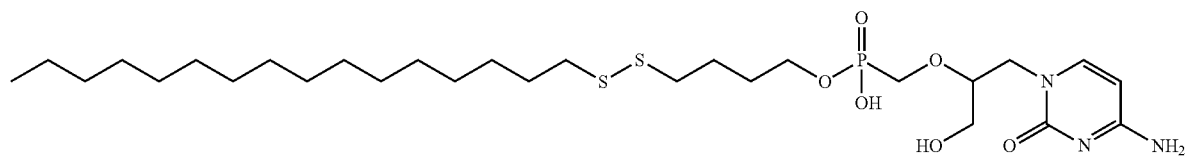 [SMILES: CCCCCCCCCCCCCCCCSSCCCCOP(=O)(O)COC(CO)Cn1ccc(N)nc1=O]

4-(hexadecyldisulfanyl)butyl hydrogen (((1-(4-amino-2-oxopyrimidin-1(2H)-yl)-3-hydroxypropan-2-yl)oxy)methyl) phosphonate or salts thereof;

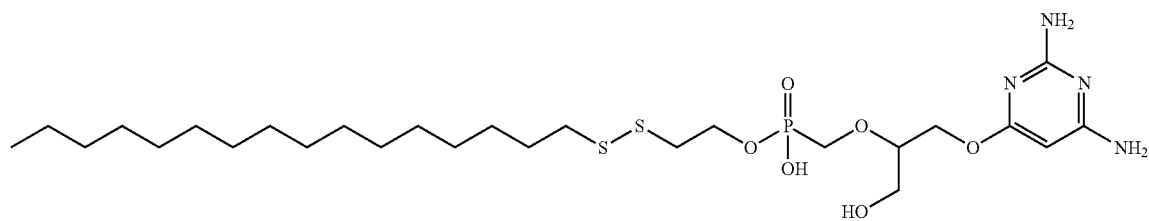 [SMILES: CCCCCCCCCCCCCCCCSSCCOP(=O)(O)COC(CO)COc1cc(N)nc(N)n1]

2-(hexadecyldisulfanyl)ethyl hydrogen (((1-((2,6-diaminopyrimidin-4-yl)oxy)-3-hydroxypropan-2-yl)oxy)methyl) phosphonate or salts thereof;

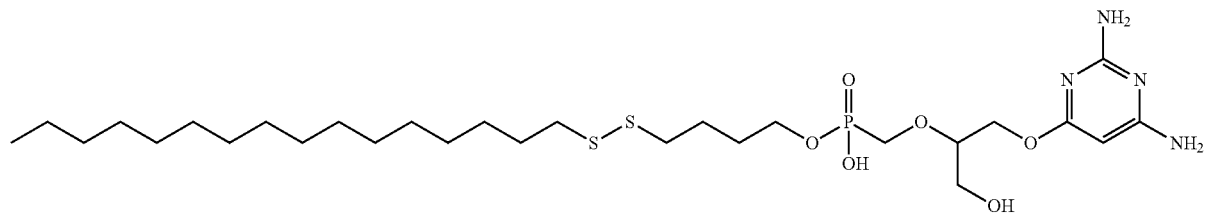 [SMILES: CCCCCCCCCCCCCCCCSSCCCCOP(=O)(O)COC(CO)COc1cc(N)nc(N)n1]

4-(hexadecyldisulfanyl)butyl hydrogen (((1-((2,6-diaminopyrimidin-4-yl)oxy)-3-hydroxypropan-2-yl)oxy)methyl) phosphonate or salts thereof;

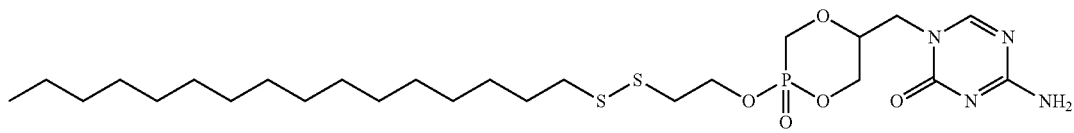 [SMILES: CCCCCCCCCCCCCCCCSSCCOP1(=O)COC(Cn2cnc(N)nc2=O)CO1]

4-amino-1-((2-(2-(hexadecyldisulfanyl)ethoxy)-2-oxido-1,4,2-dioxaphosphinan-5-yl)methyl)-1,3,5-triazin-2(1H)-one or salts thereof;

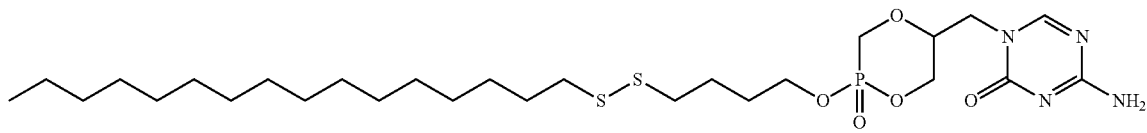 [SMILES: CCCCCCCCCCCCCCCCSSCCCCOP1(=O)COC(Cn2cnc(N)nc2=O)CO1]

4-amino-1-((2-(4-(hexadecyldisulfanyl)butoxy)-2-oxido-1,4,2-dioxaphosphinan-5-yl)methyl)-1,3,5-triazin-2(1H)-one or salts thereof;

Methods of Preparation

Preparation of compounds disclosed herein may be prepared using procedures as outlined in the Figures. In certain embodiments, the disclosure relates to methods of preparing compounds of Formula A comprising mixing the following compounds,

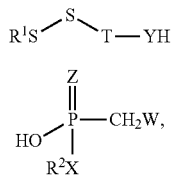

Formula WA

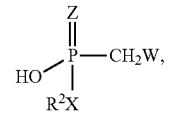

Formula WB under conditions such that a compound of Formula A is formed,

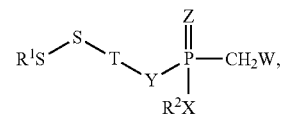

Formula A wherein the substitutents T, W, X, Y, Z, $R^1$ and $R^2$ are reported herein.

In certain embodiments, the disclosure relates to methods of preparing compounds of formula WC comprising mixing the following compounds,

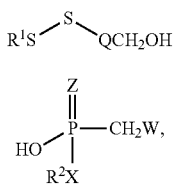

Formula WD

Formula WB under conditions such that a compound of formula WC is formed,

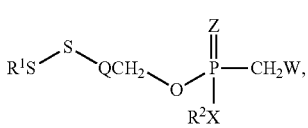

Formula WC wherein the substituents, e.g., T, W, X, Z, $R^1$ and $R^2$ are reported herein.

In certain embodiments, the disclosure relates to methods of preparing compounds of formula WE comprising mixing the following compounds,

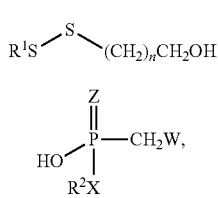

Formula WF

Formula WB under conditions such that a compound of formula WE is formed,

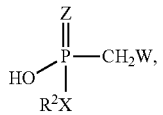

Formula WE wherein the substituents, e.g., n, W, X, Z, $R^1$ and $R^2$ are reported herein.

Methods of Use

In certain embodiments, the disclosure relates to methods of treating or preventing a viral infection or cancer comprising administering in effective amount of a compound disclosed herein to a subject in need thereof. In some embodiments, the subject is at risk of, exhibiting symptoms of, suffering from, or diagnosed with a viral infection.

In some embodiments, the subject is at risk of, exhibiting symptoms of, or diagnosed with influenza A virus including subtype H1N1, influenza B virus, influenza C virus, rotavirus A, rotavirus B, rotavirus C, rotavirus D, rotavirus E, SARS coronavirus, Respiratory syncytial virus (RSV), human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In certain embodiments, the viral infection is an alphavirus, flavivirus or coronaviruses orthomyxoviridae or paramyxoviridae, Powassan virus or filoviridae. In certain embodiments, the viral infection is selected from MERS coronavirus, Eastern equine encephalitis virus, Western equine encephalitis virus, Venezuelan equine encephalitis virus, Ross River virus, and Chikungunya virus.

In certain embodiments, methods disclosed herein are contemplated to be administered in combination with other the antiviral agent(s) such as abacavir, acyclovir, adefovir, amantadine, amprenavir, ampligen, arbidol, atazanavir, atripla, boceprevir, cidofovir, combivir, complera, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, stribild, tenofovir, tenofovir disoproxil, tenofovir alafenamide fumarate, tipranavir, trifluridine, trizivir, tromantadine, truvada, valaciclovir, valganciclovir, vicriviroc, vidarabine, viramidine, zalcitabine, zanamivir, or zidovudine, and combinations thereof.

In certain embodiments, the disclosure contemplates the treatment or prevention of a viral infection using compounds disclosed herein, wherein viral infection is human immunodeficiency virus or hepatitis B virus.

In certain embodiments, the disclosure relates to methods of treating cancer comprising administering in effective amount of a compound disclosed herein to a subject in need thereof.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genitourinary apparatus and, more particularly, childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the oesophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, tricoleukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, phaeochromocytoma, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

In certain embodiments, this disclosure contemplates administering compounds reported herein in combined with another chemotherapy regimen or anticancer agent.

A "chemotherapy agent," "chemotherapeutic," "anti-cancer agent" or the like, refer to molecules that are recognized to aid in the treatment of a cancer. Contemplated examples include combinations such as a compound disclosed herein and cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); rituximab, cyclophosphamide, doxorubicin, vincristine, prednisolone (RCHOP); bleomycin, etoposide, cisplatin (BEP); epirubicin, cisplatin, 5-fluorouracil (ECF); or epirubicin, cisplatin, capecitabine (ECX); methotrexate, vincristine, doxorubicin, cisplatin (MVAC).

In certain embodiments, the anti-cancer agent selected from abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof.

In certain embodiments, the chemotherapy agent is an anti-PD-1, anti-CTLA4 antibody or combinations thereof, such as an anti-CTLA4 (e.g., ipilimumab, tremelimumab) and anti-PD1 (e.g., nivolumab, pembrolizumab, atezolizumab, avelumab, durvalumab). In certain embodiments, the method of administration is in a subject with a lymphodepleted environment. In certain embodiments, lymphodepleting agents (e.g., cyclophosphamide and fludarabine)

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include, but are not limited to, the ammonium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

Pharmaceutical compositions for use in the present disclosure typically comprise an effective amount of a compound and a suitable pharmaceutically acceptable carrier. The preparations may be prepared in any manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778; 6,369,086; 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound of the present disclosure and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300, 400 or 500 mg per unit dosage.

The compounds can be administered by a variety of routes including the oral, ocular, rectal, transdermal, subcutaneous, intravenous, intramuscular or intranasal routes, depending mainly on the specific preparation used. In certain embodiments, the compound is administered by inhalation through the lungs.

The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778; 6,369,086; 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, nanoparticles, aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

In certain embodiments, the pharmaceutical composition comprises a compound disclosed herein and a propellant. In certain embodiments, an aerosolizing propellant is compressed air, ethanol, nitrogen, carbon dioxide, nitrous oxide, hydrofluoroalkanes (HFAs), 1,1,1,2,-tetrafluoroethane, 1,1,1,2,3,3,3-heptafluoropropane or combinations thereof.

In certain embodiments, the disclosure contemplates a pressurized or unpressurized container comprising a compound herein. In certain embodiments, the container is a manual pump spray, inhaler, meter-dosed inhaler, dry powder inhaler, nebulizer, vibrating mesh nebulizer, jet nebulizer, or ultrasonic wave nebulizer.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and processes for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers", are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or non-ionic surface active agents. Suitable anionic surfactants include, but are not limited to, those containing carboxylate, sulfonate and sulfate ions. Non-limiting examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include, but are not limited to, ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include, but are not limited to, sodium N-dodecyl-β-alanine, sodium N-lauryl-β-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulated for modified or controlled release. Examples of controlled release dosage forms include, but are not limited to, extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit® In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., compound, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compound described herein can be administered adjunctively with other active compounds. These compounds include, but are not limited to, analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compound can be administered in the same dosage form or in separate dosage forms with one or more other active agents.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

The present disclosure will now be described with reference to the following non-limiting Examples.

EXPERIMENTAL

Synthesis

Figure 4A:
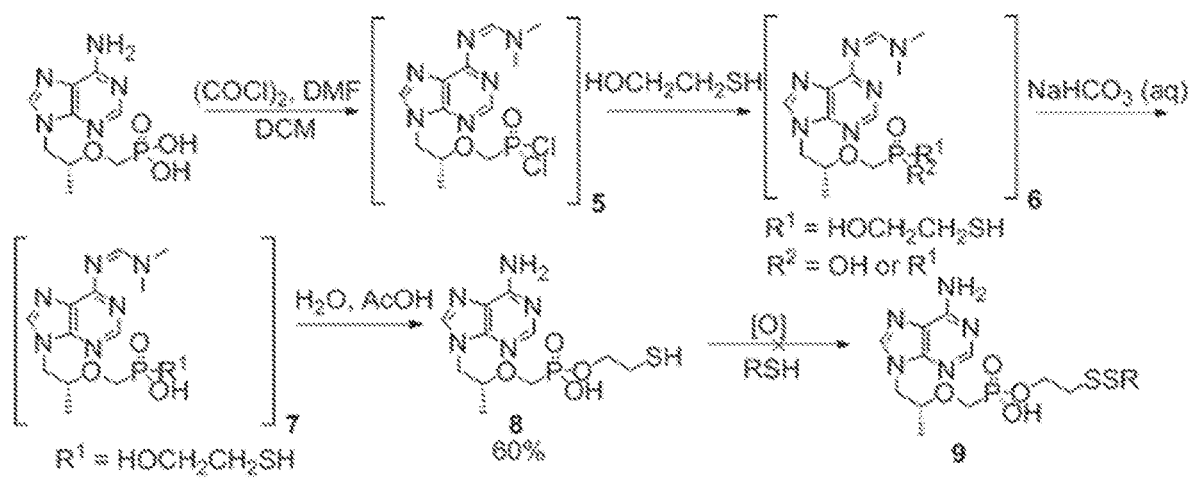
FIG. 4a illustrates a first synthetic strategy for some embodiments of this disclosure.
Figure 4B:
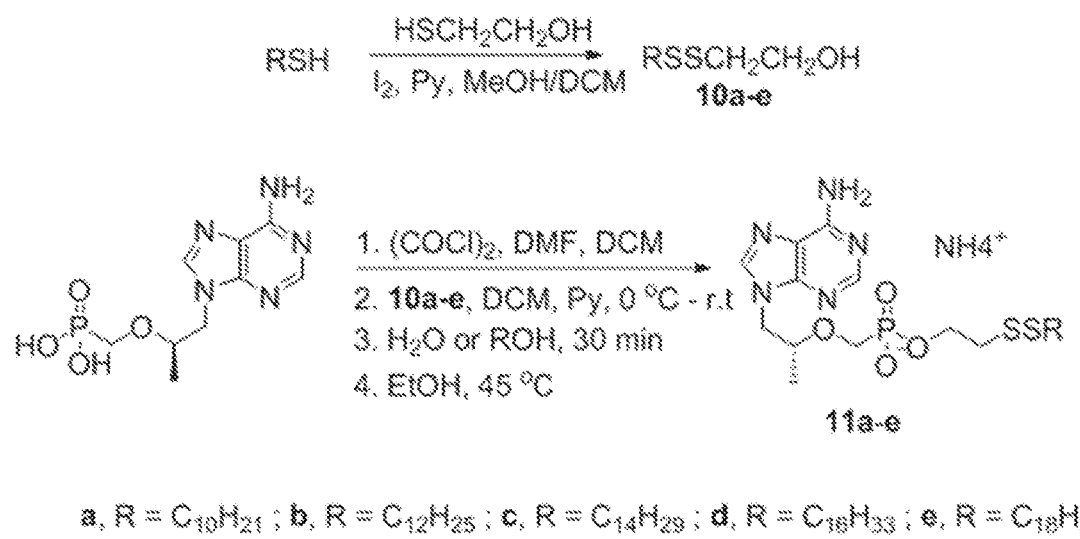
FIG. 4b illustrates a second synthetic strategy for some embodiments of this disclosure.

As illustrated in FIG. 4a, synthesis toward TFV disulfide conjugates began with commercially available TFV (CombiBlocks) that were converted to the bis-chloride with excess oxalyl chloride and DMF in dichloromethane (DCM). When catalytic DMF was used, the reaction stalled due to the presence of the C-6 amino moiety on the purine ring system which depletes the catalytic Vilsmeyer chlorinating agent and becomes concomitantly protected as N-formimidine. This was resolved by adding 1.2 equivalents of DMF to rapidly afford the formimidine protected bis-chloridate that was subsequently treated with excess β-mercaptoethanol to generate a mixture of bis- and mono-adducts of compound 6, which were not isolated. When compound 6 was stirred with aqueous saturated sodium bicarbonate for 30 minutes, the complexity of the mixture reduced to a single species whose m/z ratio was consistent with compound 7. Acid-mediated hydrolysis of compound 7 afforded compound 8 in moderate yield, whose structural assignment was unambiguously characterized by HRMS, $^1$H, $^{13}$C, and $^{31}$P NMR spectroscopy. A key step of the synthesis involved the construction of the critical disulfide linkage between compound 8 and hexadecanethiol. Unfortunately, this endeavor proved unsuccessful with a variety of oxidizing agents including iodine, oxone, $O_2$, and $H_2O_2$. Cyclization of the mercaptoethanol linker was observed when compound 8 reacted with molecular iodine, and unidentifiable by-products or no appreciable reaction occurred with the latter oxidants. An alternative synthesis was then sought (as illustrated in FIG. 4b). To this end, β-mercaptoethanol was pre-oxidized with a handful of $C_{10}$-$C_{18}$ aliphatic thiols to produce the corresponding disulfide-bridged linkers 10a-e in moderate yields of 34-45%. These compounds were crystalline solids with sharp melting points (compound 10a is an oil) that could be cleanly purified by silica gel column chromatography. Alcohols 10a-e were subsequently coupled to TFV using the same DMF/oxalyl chloride methodology (shown above in FIG. 4a) to afford monoesters 11a-e in yields of 12-49% after hydrolysis of the remaining chloridate with water and deprotection of formimidine in warm ethanol.

Despite the installation of a greasy hydrocarbon tail, the exposed phosphonic acid moiety retained significant polarity that initially plagued normal phase chromatographic purification of compounds 11a-e on silica gel. Relatively polar solvent gradients of DCM/MeOH/$NH_4$OH (80:20:0.1) failed to move these compounds on aluminum-backed silica TLC plates and increasing the percentage of methanol compromised the integrity of the silica and promoted streaking. However, when the concentration of ammonium hydroxide was raised from 0.1 to 1-3% (v/v), appreciable movement was observed by TLC and these conditions were successfully applied to column chromatography to furnish compounds 11a-e as their ammonium salts, as determined by elemental analysis.

With monoesters 11a-e in hand, the corresponding bis-disulfides 12a-e (shown in FIG. 5) were prepared employing the same protocol and using two equivalents of compounds 10a-e during coupling to TFV instead of one. All five transformations occurred as predicated to afford compounds 12a-e in 30-40% yield after purification without incident.

Figure 5:
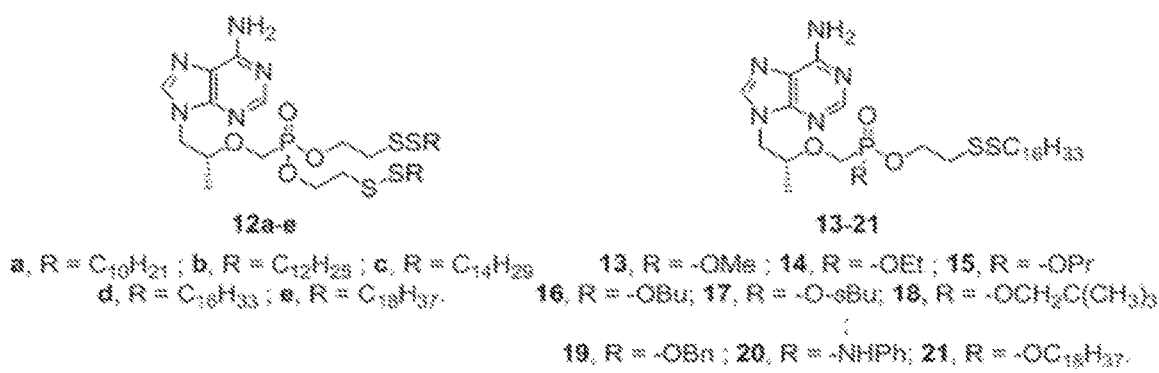
FIG. 5 illustrates further embodiments of this disclosure.

A series of mixed phosphonodiesters (compounds 13-21) were synthesized and are also displayed in FIG. 5. The synthesis of these compounds was done using compound 10d as the coupling lipid and various alcohols/amines to quench the remaining phosphonochloridate in step 3 of the reaction scheme shown in FIG. 4b, rather than water. Note that compounds 13-21 were prepared as an inconsequential mixture of diastereomers and were not separated.

Figure 6:
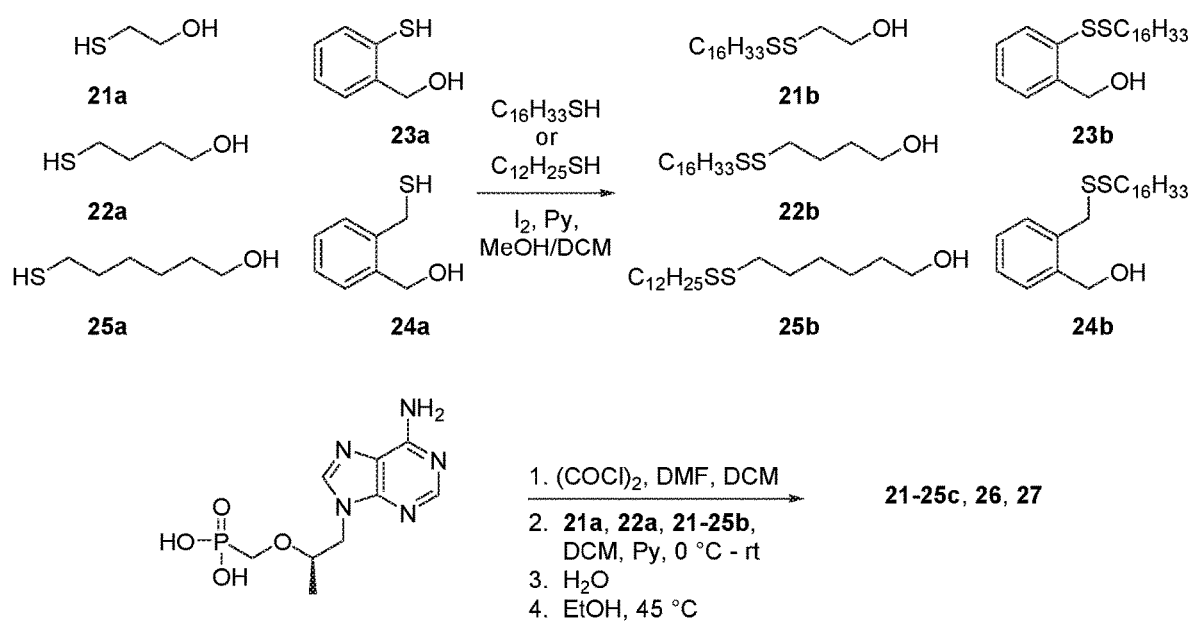
FIG. 6 illustrates methods for preparing further embodiments of this disclosure.

As illustrated in FIG. 6, conjugates 21-25c, 26, and 27 were also prepared. Hexadecanethiol was oxidized with thiols 21-25a in the presence of iodine to furnish lipids 21-25b as low-melting point solids that were purified via column chromatography. Compounds 21-25b were then coupled to TFV with oxalyl chloride and DMF to afford the corresponding conjugates 21-25c after formimidine deprotection and purification on silica gel using a DCM:MeOH:$NH_4$OH gradient. Both compounds 26 and 27 were purified on a C18 reverse phase column and were isolated as free acids following lyophilization. The structures of compounds 21-25c, 26, and 27 are presented in Table 3.

Antiviral Activity

Compounds synthesized were evaluated against HIV-infected PBMCs and antiviral activity was assessed by measuring reverse transcriptase in cell supernatants. Compounds 11a-e, 12a-e, and 13 were assayed against HBV and qPCR was used to quantify viral DNA following incubation in HepG2.2.15 cells after 6 days. Table 1 details the antiviral activity of conjugates 11a-e with modifications to the lipid tail.

TABLE 1

HIV-1 and HBV Activity of Lysogenic Phospholipids
11a-e Compared to TDF, CMX-157, and DTE-TFV

| | HIV-1 | | | HBV | | |
|---|---|---|---|---|---|---|
| Compound | $EC_{50}{}^{b}$ (PBMCs) | $CC_{50}{}^{c}$ (PBMCs) | TI ($CC_{50}/EC_{50}$) | $EC_{50}{}^{b}$ (HepG2) | $CC_{50}{}^{c}$ (HepG2) | TI ($CC_{50}/EC_{50}$) |
| TDF | 0.0046 | 43.7 | 9,500 | 0.34 | 64.5 | 190 |
| TFV | 0.319 | >100 | >300 | — | — | — |
| 8 | 18.6 | >100.0 | >5.38 | 41.9 | >100.0 | >2.4 |
| DTE-TFV | 1.61 | >100.0 | >62.1 | 11.6 | >100.0 | >8.6 |
| 11a | 0.085 | >50.0 | >590 | >50.0 | >50.0 | >1 |
| 11b | 0.0030 | 25.0 | 8,300 | 1.67 | >50.0 | >30 |
| 11c | 0.00050 | 14.0 | 28,000 | 0.444 | >25 | >56 |
| 11d | 0.00065 | 14.3 | 22,000 | 0.020 | >25 | >1250 |
| CMX-157 | 0.02 | >100.0 | >5000 | — | — | — |
| 11e | 0.00060 | 6.36 | 11,000 | 0.505 | >50 | >50 |

Data represent an average of triplicate experiments.
[b]$EC_{50}$, effective concentration (in μM) required to inhibit HIV-1 or HBV by 50%.
[c]$CC_{50}$, effective concentration (in μM) required to reduce the viability of uninfected cells by 50%.

These compounds resemble lysogenic phospholipids characterized by an anionic phosphate head group and a single aliphatic tail. This structural motif confers a conical-like shape that facilitates facile translocation between the inner and outer leaflets of the plasma membrane and procures detergent-like properties that disrupts lipid bi-layers. As shown in Table 1, compound 11a possesses the shortest lipid ($C_{10}$) and is 18-fold less potent than TDF (85 nM vs. 4.6 nM) with a relatively poor therapeutic index (TI) of 590 at the $EC_{50}$. Extending the length of the alkyl chain by two carbon atoms results in compound 11b whose HIV-1 activity (3.0 nM) is comparable to TDF and seven-fold more active than CMX-157 (20 nM). Maximum antiviral activity was obtained for conjugates 11c-e with alkyl chain lengths ranging from 14-18 carbon atoms, respectively. Compounds 11c-e exhibit sub-nanomolar $EC_{50}$ values of ~0.5 nM that outrivals TDF and CMX-157 and compound 11d boasts a $TI_{50}$ that exceeds 20,000 whereas that of compound 11c approaches 30,000. This broad therapeutic window is sustained even at the $EC_{90}$ for both compounds 11c and 11d and is nearly an order of magnitude wider than the $TI_{90}$ of TDF (11,000 vs. 1,300—data not shown). Note that compounds 11c-e possess linker lengths of 19, 20, and 21 atoms, respectively, when the mercaptoethanol bridge is taken into account. Table 1 also reveals that increasing chain length is associated with a concomitant increase in cytotoxicity, a phenomenon that has been well-documented for a variety of surfactants in numerous aquatic organisms.

With respect to HBV activity, all conjugates in Table 1 demonstrated rather unremarkable activity with the exception of compounds 11d whose potency (20 nM) and TI (1250) bested that of TDF which further supports the advantage of reduction-sensitive lipids over carbonate prodrug strategies.

In addition to compounds 11a-e, DTE-TFV and 8 were also assessed in this assay and were found to be 5- and 58-fold less active than TFV against HIV-1, respectively. The dramatic potency loss observed for compound 8 is interesting given that this compound is predicated to readily undergo intramolecular cyclization to release the bound nucleoside in vivo. Without wishing to be limited to any particular theory, it is suspected that the β-mercaptoethanol linker resists cleavage following intracellular delivery and obstructs the phosphorylation of the parent nucleoside to the active diphosphate.

In contrast to compounds 11a-e, compounds 12a-e resemble conventional phospholipids with two aliphatic tails that assume a cylindrical shape and do not readily traverse the plasma membrane on their own accord. Phosphonodiesters in Table 2 proved to be less potent than compounds 11a-e.

TABLE 2

HIV-1 and HBV Activity of Bis-disulfide Conjugates 12a-e

| | HIV-1 | | | HBV | | |
|---|---|---|---|---|---|---|
| Compound | $EC_{50}{}^{b}$ (PBMCs) | $CC_{50}{}^{c}$ (PBMCs) | TI ($CC_{50}/EC_{50}$) | $EC_{50}{}^{b}$ (HepG2) | $CC_{50}{}^{c}$ (HepG2) | TI ($CC_{50}/EC_{50}$) |
| TDF | 0.0046 | 43.7 | 9,500 | 0.34 | 29.2 | 86 |
| 12a | 0.349 | >100.0 | >287 | >100 | >100.0 | >1 |
| 12b | 1.18 | >100.0 | >85.0 | >100 | >100.0 | >1 |
| 12c | 0.189 | >100.0 | >529 | >100 | >100.0 | >1 |
| 12d | 6.32 | >25 | 4.0 | >25 | >25 | >1 |
| 12e | 0.331 | >25 | >76 | >25 | >25 | >1 |

Data represent an average of triplicate experiments.
[b]$EC_{50}$, effective concentration (in μM) required to inhibit HIV-1 or HBV by 50%.
[c]$CC_{50}$, effective concentration (in μM) required to reduce the viability of uninfected cells by 50%.

Conjugates 12a and 12e achieved potencies comparable to TFV against HIV-1 whereas compound 12c was the only compound to demonstrate a two-fold increase in activity when compared to the parent nucleoside.

Tested compounds were relatively inactive against HBV relative to TDF. The translocation of compounds 12a-e from the outer leaflet to inner leaflet of the plasma membrane is required in order for TFV to blockade reverse transcriptase located within the cytosol. If it is assumed that reduction is facile upon entry and that compounds 11a-e and 12a-e interact with the cellular machinery following cleavage of the linker, then the results presented in Table 2 strongly implicate membrane translocation as the rate-limiting step governing the $EC_{50}$ value of compounds 12a-e. It is therefore interesting that compounds 12a, c and e and TFV (Table 2) all have strikingly similar HIV-1 activity despite their disparate alkyl chain lengths and in the case of TFV, no chain at all.

Conjugates 22-24c (as illustrated in FIG. 6 and Table 3) were evaluated against HIV-1 infected PBMCs and chronically HBV-infected hepatocytes. TFV and TDF were also evaluated and serve as reference compounds to assess the efficacy of this prodrug strategy. Thiols 22-24a were judiciously selected based on commercial availability and their propensity for cyclization when the hydroxyl moiety bears a potential leaving group (i.e. TFV). Note that compound 23a is expected to undergo o-thioquinone methide formation rather than intramolecular cyclization. As shown in Table 3, both compounds 22c and 24c have similar HIV-1 activity to conjugate 21c (~0.5 nM). However, compound 22c is significantly less cytotoxic than compounds 21c and 24c ($CC_{50}$>50 µM). An accurate determination of the $CC_{50}$ for compound 22c was not possible due to precipitation at concentrations higher than 50 µM. Nonetheless, the attenuated toxicity of compound 22c combined with its potent antiviral activity achieves a $TI_{50}$ in excess of 100,000 providing a relatively non-toxic disulfide bearing lipid prodrug of TFV.

TABLE 3

HIV-1 and HBV Activity of Conjugates 21-25c, 26, and 27 Compared to TFV and TDF

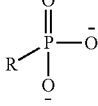

| Id. | Structure | HIV-1 | | | HBV | | |
| --- | --- | --- | --- | --- | --- | --- | --- |
| | | $EC_{50}^{b}$ (PBMCs) | $CC_{50}^{c}$ (PBMCs) | TI ($CC_{50}/EC_{50}$) | $EC_{50}^{b}$ (HepG2) | $CC_{50}^{c}$ (HepG2) | TI ($CC_{50}/EC_{50}$) |
| TFV | 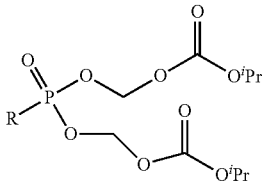 | 0.320 | >100 | >300 | — | — | — |
| TDF | 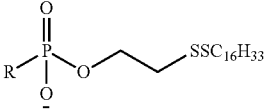 | 0.0045 | 44.0 | 9,500 | 0.34 | 64.5 | 190 |
| 21c | 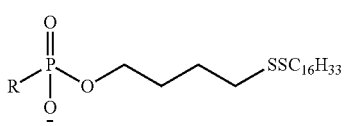 | 0.00065 | 14.3 | 22,000 | 0.020 | >25 | >1200 |
| 22c | 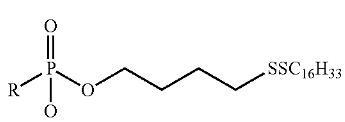 | <0.0005 | >50 | >100,000 | 0.248 | >50 | >200 |
| 23c | 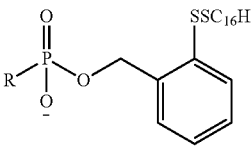 | 0.0229 | 17.2 | 751 | 4.48 | 17.5 | 3.9 |

TABLE 3-continued

HIV-1 and HBV Activity of Conjugates 21-25c, 26, and 27 Compared to TFV and TDF R = [adenine-linked (R)-9-[2-(phosphonomethoxy)propyl] group, i.e., tenofovir scaffold attached via O-CH-CH₃]

| Id. | Structure | HIV-1 EC$_{50}$[b] (PBMCs) | HIV-1 CC$_{50}$[c] (PBMCs) | HIV-1 TI (CC$_{50}$/EC$_{50}$) | HBV EC$_{50}$[b] (HepG2) | HBV CC$_{50}$[c] (HepG2) | HBV TI (CC$_{50}$/EC$_{50}$) |
|---|---|---|---|---|---|---|---|
| 24c | R-P(=O)(O⁻)-O-CH₂-(o-C₆H₄)-CH₂-SSC₁₆H₃₃ | <0.0005 | 15.9 | >31,800 | 0.152 | 32.5 | 214 |
| 25c | R-P(=O)(O⁻)-O-(CH₂)₄-SSC₁₂H₂₅ | 0.007 | >50 | >7000 | 1.05 | >50 | >47 |
| 26 | R-P(=O)(OH)-O-CH₂CH₂-SH | 18.6 | >100 | >5.38 | 41.9 | >100 | >2 |
| 27 | R-P(=O)(OH)-O-(CH₂)₄-SH | 5.13 | >100 | >18 | >100 | >100 | >1 |

Data represent an average of triplicate experiments. [b]EC$_{50}$, effective concentration (in μM) required to inhibit HIV-1 or HBV by 50%. [c]CC$_{50}$, effective concentration (in μM) required to reduce the viability of uninfected cells by 50%.

Stability Studies

In order to be considered clinical candidates for oral delivery, conjugates 11b-e must demonstrate sufficient hydrolytic, nucleophilic, and plasma stability. Bis(DTE)-conjugates have dismal reported plasma stability profile of ($t_{1/2}$<5 min). Compound 11c and 11d were selected as model compounds and subjected to various media including human serum, PBS buffer (pH 7.4), Dulbecco's Modified Eagle Medium (DMEM), and carbonate/bicarbonate buffer (pH 9). Aliquots of each sample were analyzed by LC-MS at varying times points over the course of 2 hours with a final time point at 24 to assess decomposition.

Both compounds 11c and 11d demonstrated robust stability in human plasma with a half-life of >24 h. In contrast, DTE-TFV readily degraded in the presence of human plasma ($t_{1/2}$=34 min) which is in agreement with previous findings.

Experiments were performed to see how compounds how compounds 11c and 11d would fare in the presence of base (pH 9), PBS (pH 7.4), and upon exposure to nucleophilic media (DMEM). Preliminary experiments with compound 11d and DTE-TFV in PBS initially revealed that compound 11 d rapidly decomposed in PBS solution with $t_{1/2}$<20 min while DTE-TFV boasted a half-life of 3.5 h. Poor PBS stability was also observed for other alkoxyalkyl conjugates in PBS, but not for less hydrophobic conjugates. In light of these observations, it was suspected that chemical decomposition was not the operative mechanism behind this phenomenon in PBS, but rather physical adsorption of the lipid to the glass surface was responsible for abstracting analyte from the solution. To this end, the stability of hexadecyloxypropyl 2'-deoxy-2'-fluorouridine, a non-labile alkoxyalkyl lipid conjugate of 2'-deoxy-2'-fluorouridine in PBS buffer using Pyrex, Kimax, and silanized glassware was assessed. These experiments revealed that both Pyrex and silanized glass encourage substantial lipid adsorption and give rise to a rapid (but artificial) decomposition profile for lipid-bound nucleosides (data not shown). Interestingly, Kimax glassware did not produce this effect despite its near identical composition to Pyrex. This prompted re-assessment of the PBS stability of the disulfide lipid conjugates in Kimax glassware. Note that all stability experiments were performed in Kimax glassware using hexadecyloxypropyl 2'-deoxy-2'-fluorouridine as an internal standard. With these conditions, both compounds 11c and 11d exhibited similar stabilities at pH 9, PBS, and DMEM. Neither compound 11c nor compound 11d exhibit a half-life of >2 h in these media which is in stark contrast to their stability in human serum (>24 h). It is believed that the precipitation of compounds 11d and 11c from the media is responsible for the poor half-life of these compounds in PBS, carbonate buffer, and DMEM. This is consistent with the observation that the $C_{14}$ chain of compound 11c procures a near two-fold stability increase over the $C_{16}$ linker of compound 11d in all examined media (with the exception of human serum). It is plausible that the proteins present in human serum provide additional Van der Waals contacts and support micelle formation to facilitate dissolution. Taken together, the inherent plasma stability of compounds 11c and 11d illuminates the possibility for selective intracellular delivery that may reduce systemic exposure of TFV or other bound cargo.

As a Tool to Probe Enzymatic Cleavage.

A subset of prodrug strategies relies on the presence of specific hydrolases such as phospholipase C or cathepsin A to sever the P—O or P—N linkages between prodrug and nucleoside. Unfortunately, little is known about the substrate specificity of these enzymes. Seminal reports by Kelly et al. concluded 5'-nucleotide phosphodiesterase preferentially cleaves aryl esters over aliphatic and benzyl derivatives. However, a systematic analysis of various ester derivatives has not been examined in PBMCs. This was seen as an opportunity to indirectly probe the enzymatic machinery responsible for the hydrolysis of TFV phosphonomonoesters in PBMCs using the reduction-sensitive lipids as a delivery vehicle.

Conjugates 13-21 were prepared using hexadecyldisulfanylethanol (HDE) as the lipid of choice. HDE ensures thorough cellular permeation and relatively rapid intracellular cleavage to expose the corresponding phosphonomonoester which is then subsequently hydrolyzed in a rate-limiting step to TFV. The rate of hydrolysis is dependent on the nature of the alkyl or aryl ester and therefore governs the HIV-1 activity of compounds 13-21. None of these compounds (13-21) exhibited antiviral activity comparable to compounds 11c-e due to the additional cleavage step (Table 4).

TABLE 4

HIV-1 Activity of Lipid Conjugates 13-21

| Compound | R- | $EC_{50}^{b}$ (PBMCs) | $CC_{50}^{c}$ (PBMCs) | TI ($CC_{50}/EC_{50}$) |
|---|---|---|---|---|
| TDF | N.A | 0.0046 | 43.7 | 9,500 |
| TFV | N.A | 0.319 | >100.0 | >300 |
| 13 | MeO— | 0.026 | 38.2 | 1,500 |
| 14 | EtO— | 0.349 | 36.2 | 104 |
| 15 | PrO— | 0.216 | 10.6 | 49.0 |
| 16 | n-BuO— | 0.19 | 27.9 | 150 |
| 17 | s-BuO— | 0.049 | 23.7 | 480 |
| 18 | $C(CH_3)_3CH_2O$— | 0.14 | >100.0 | >700 |
| 19 | $PhCH_2O$— | 0.018 | 41.1 | 2,300 |
| 20 | PhNH— | 0.005 | 34.2 | 7,000 |
| 21 | $C_{18}H_{37}O$— | 0.911 | >50.0 | >50 |

Data represent an average of triplicate experiments.
[b]$EC_{50}$, effective concentration (in µM) required to inhibit HIV-1 or HBV by 50%.
[c]$CC_{50}$, effective concentration (in µM) required to reduce the viability of uninfected cells by 50%.

Successively increasing the chain length of the alkyl ester from methyl to n-Bu resulted in significant potency loss with compound 13 being the most active (26 nM) of the linear series (compounds 13-15, 16 and 21). When compound 13 is omitted, HIV-1 activity concomitantly increased with chain length from ethyl to n-Bu. Data suggests that cleavage of methyl monoester 13 in human PBMCs is superior to the corresponding ethyl, propyl, and n-butyl esters (14, 15, 16, respectively) and that conversion to TFV increases with chain length for this series. Note that the antiviral activity of compounds 13-21 directly corresponds to TFV and thus provides an indirect readout for the concentration of the free nucleoside.

Longer alkyl chains impose significant phospholipid character with the HDE linker and become "stuck" in the plasma membrane—a phenomenon observed with conjugates 12a-e. The activity of compound 21 (0.911 µM) is likely plagued by the same phenomenon and obscures the relationship between the $EC_{50}$ and enzymatic cleavage of the octyl ester. Fortunately, the remaining esters in Table 4 are sufficiently smaller than the HDE linker and do not exhibit this behavior.

Conjugates 16, and 17-18 reveal that a moderate increase in steric encumbrance around the phosphonate center correlates with an increase in antiviral activity. The s-Bu ester 17 is superior to its n-Bu analogue 16 by nearly four-fold. The neopentyl derivative 18 had unimpressive activity of 0.14 µM although the corresponding n-pentyl ester was not synthesized for comparison.

Aryl phosphonoamidate 20 and benzyl ester 19 are the most potent compounds in Table 4 (5 nM and 18 nM, respectively) which is consistent with the notion that aryl and benzyl esters are superior substrates over their alkyl counterparts.

The invention claimed is:
1. A compound of Formula I,

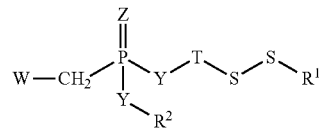

Formula I or salt thereof wherein,
W is

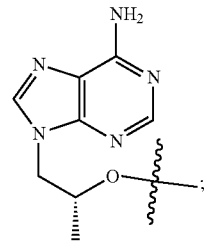 [SMILES: *O[C@H](C)Cn1cnc2c(N)ncnc21]

Z is selected from O, S, or Se;
Y is selected from O, S, or NH;
T is an aryl or alkyl linking group,
$R^1$ a saturated hydrocarbon chain having 6 or more carbon atoms;
$R^2$ is $R^1$SST-, hydrogen, alkyl, aryl, phenyl, 4-fluorophenyl, 4-chlorophenyl, 4-bromophenyl, naphthyl, or heterocyclyl, wherein $R^2$ is optionally substituted with one or more, the same or different, $R^{10}$;
$R^{10}$ is deuterium, alkyl, alkenyl, alkynyl, alkanoyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, benzyl, benzoyl, carbocyclyl, aryl, or heterocyclyl, wherein $R^{10}$ is optionally substituted with one or more, the same or different, $R^{11}$; and $R^{11}$ is deuterium, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, carbocyclyl, aryl, or heterocyclyl.

2. The compound of claim 1, wherein T is a $C_2$ to $C_6$ alkyl.

3. The compound of claim 1, wherein Z and Y are each O.

4. The compound of claim 1, wherein $R^1$ is a $C_6$ to $C_{20}$ lipid.

5. The compound of claim 1, wherein $R^2$ is $R^1SST$-, hydrogen, alkyl, aryl or phenyl.

6. The compound of claim 1, wherein $R^2$ is hydrogen, methyl, or alkyl.

7. The compound of claim 1, selected from the following compounds as free acids or salts thereof:

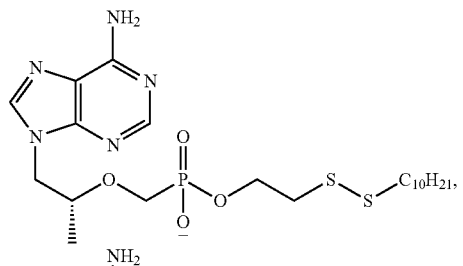

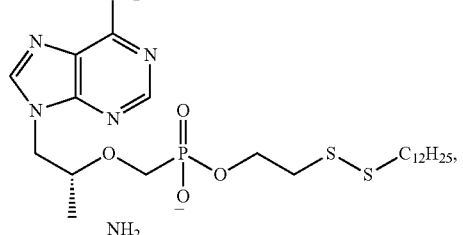

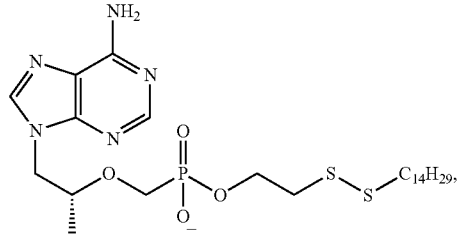

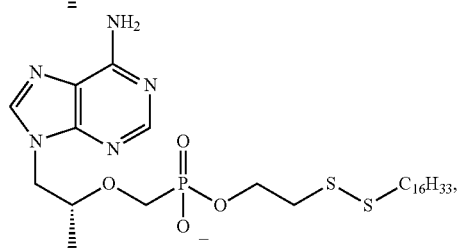

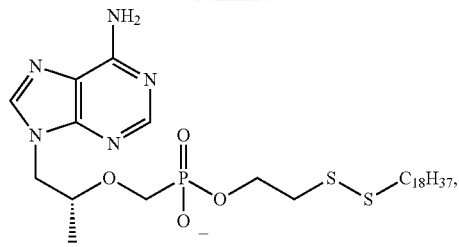

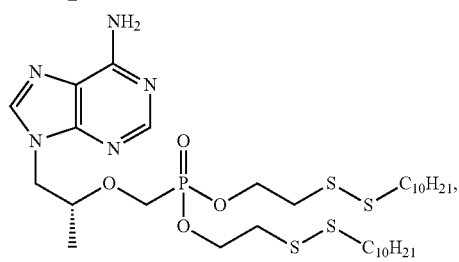

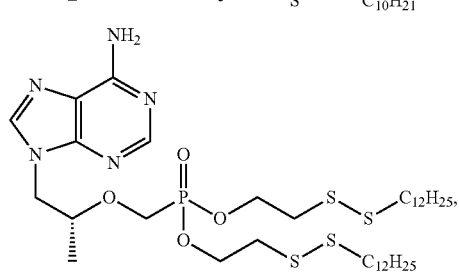

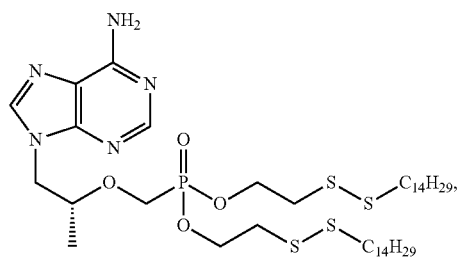

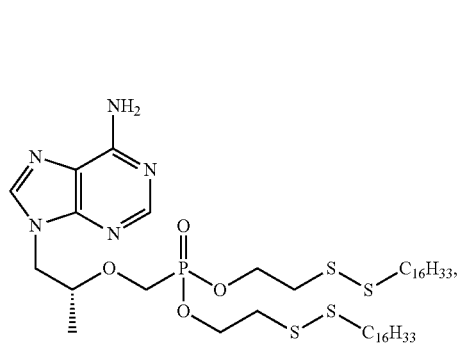

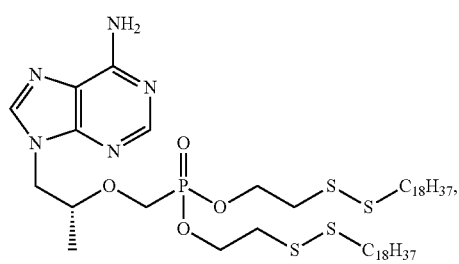

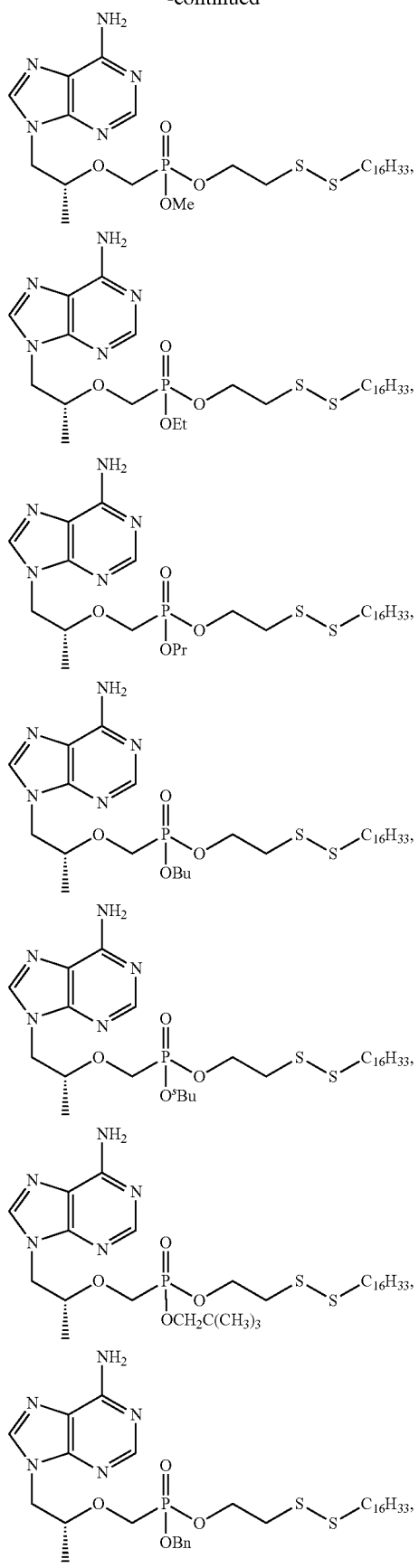
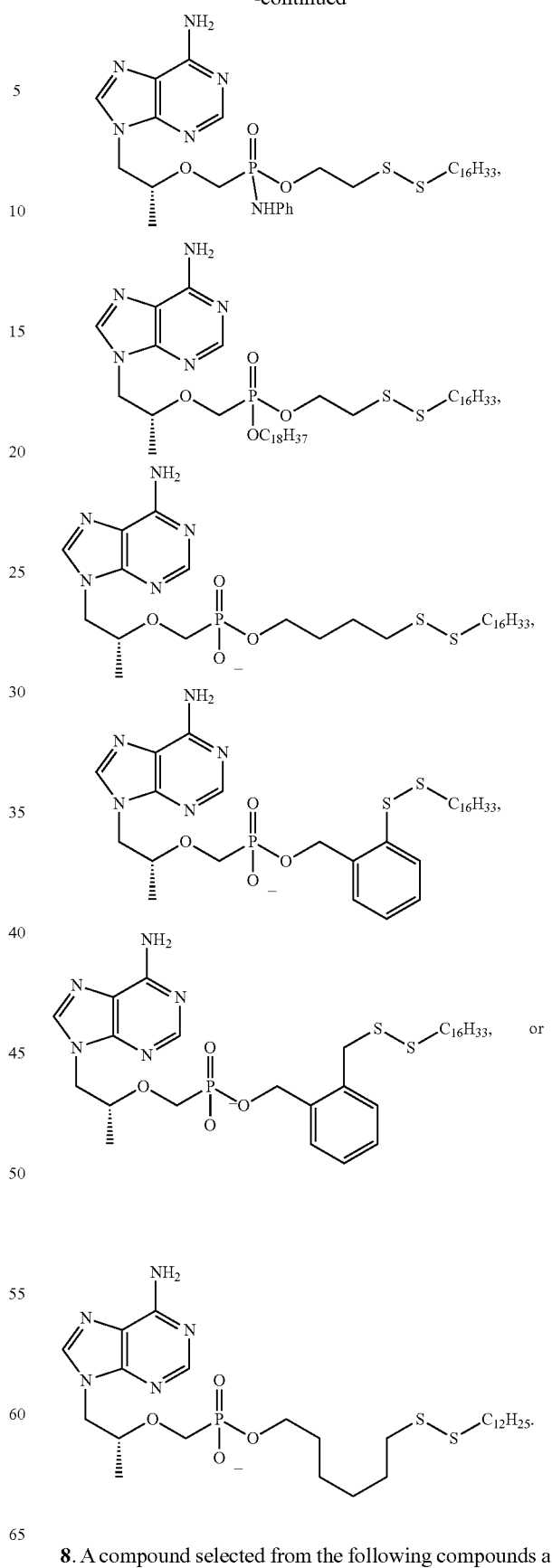
8. A compound selected from the following compounds as free acids or salts thereof:

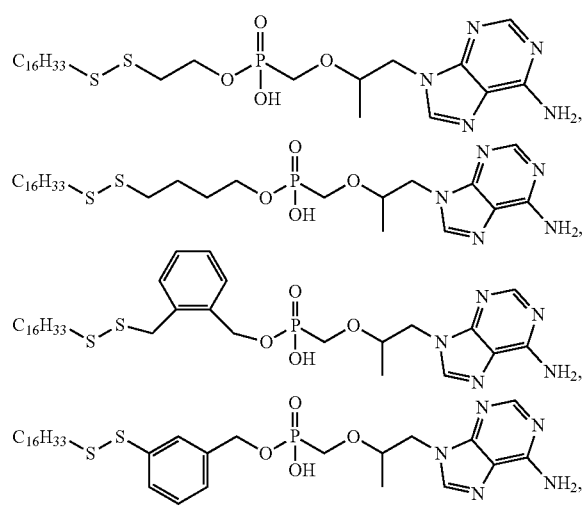

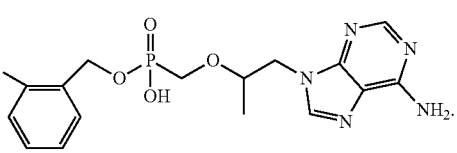

9. A pharmaceutical composition comprising a compound of claim 1 or pharmaceutically acceptable salt thereof and a pharmaceutically acceptable excipient.

10. The pharmaceutical composition of claim 9 in the form of a tablet, capsule, pill, gel, or granules.

11. The pharmaceutical composition of claim 9 in the form of an aerosol, aqueous buffer or emulsion.

12. The pharmaceutical composition of claim 1 wherein the compound is in a nanoparticle or a liposome.

* * * * *